United States Patent [19]
Toyoshima et al.

[11] Patent Number: 5,874,247
[45] Date of Patent: Feb. 23, 1999

[54] PROTEIN DISULFIDE ISOMERASE AND METHOD OF USING

[75] Inventors: Kumao Toyoshima, Setagaya; Ryuya Horiuchi, Seta-gun; Kiyoshi Yamauchi, Shizuoka; Tadashi Yamamoto, Yokohama; Koichi Igarashi, Kyoto, all of Japan

[73] Assignee: Takeda Chemical Industries, Ltd., Osaka, Japan

[21] Appl. No.: 882,877

[22] Filed: Jun. 26, 1997

Related U.S. Application Data

[63] Continuation of Ser. No. 982,138, Nov. 25, 1992, Pat. No. 5,700,678, which is a continuation of Ser. No. 635,812, Jan. 2, 1991, abandoned, which is a continuation of Ser. No. 199,307, May 26, 1988, abandoned.

[30] Foreign Application Priority Data

| Jun. 1, 1987 | [JP] | Japan | 62-138628 |
| Sep. 18, 1987 | [JP] | Japan | 62-235492 |
| Oct. 5, 1987 | [JP] | Japan | 62-251144 |

[51] Int. Cl.$^6$ .............. C12N 1/21; C12N 9/90; C12N 15/61
[52] U.S. Cl. ............ 435/69.1; 435/69.1; 435/71.2; 435/189; 435/233; 435/252.33; 530/350
[58] Field of Search ................. 435/69.1, 71.2, 435/233, 252.3, 252.33; 530/350; 536/23.2, 23.5; 935/49

[56] References Cited

U.S. PATENT DOCUMENTS

| 4,904,602 | 2/1990 | Pigiet et al. | 435/191 |
| 5,578,466 | 11/1996 | Hayano et al. | 435/69.7 |

OTHER PUBLICATIONS

Kurokawa et al., *NAR*, 11:3077–3085 (1983).
Itoh et al., *Biochem. Biophys, Res. Com.*, 138:268–274 (1986).
Edman et al., *Nature*, 317:267–270 (1985).
Pihlajaniemi et al., *The EMBO Journal*, 6(3):643–694 (1987).
Cheng et al., *The Journal of Biological Chemistry*, 262(23):11221–11227 (1987).
Yamauchi et al., *Biochemical and Biophysical Research Communications*, 146(3):1485–1492 (1987).
Pieiet et al., *Proc. Natl. Acad. Sci. USA*, 83:7643–7647 (1986).

*Primary Examiner*—George C. Elliott
*Assistant Examiner*—Thomas G. Larson
*Attorney, Agent, or Firm*—David G. Conlin; Peter F. Corless; Dike, Bronstein, Roberts & Cushman, LLP

[57] ABSTRACT

Protein disulfide isomerase, which catalyzes the exchange reaction between sulfhydryl and disulfide in a protein for formation of the most stable natural type disulfide bonds, is useful for formation of natural type disulfide bonds in a protein which is produced in a prokaryotic cell.

6 Claims, 14 Drawing Sheets

GCGGGGGAGTGCGGGAACAAAAATATCG

GTCAAAGCCGGATTATAGATCCCTTTGGCGTCACCATTGCGGCAGCGTCAGAAATGCCTG

CACTCATTATGGCGGAAGTGACGCCCGAACGTGTGCGTCAGGTGCGCGCGCAACTGCCCG

TCTTAAACAACCGTCCGCTTTGCGCCGCCGCATTTTTTTACTCGGCGCTTGATTATTATG

ATGATTCACCTTGTTACAGATTGCTATTGTGTGCGCGCGTCGAATGACCGTTAATATTCT

CTGGTTTTTAAGGCGCGTTCTGTTGCCGGTTATATGTCAAGAAGGTATCTATGGGTGAGA

TTAGTATTACCAAACTGCTGGTAGTTGCGGCGCCAACTGAAGCGCCGCGTCTGTGCCGAC

```
ATGCTGCGCCGCGCTCTGCTCTGCCTGGCCCTGACCGTCCTATTCCGCGCGGGTGCCGGC
MetLeuArgArgAlaLeuLeuCysLeuAlaLeuThrValLeuPheArgAlaGlyAlaGly
-20                          -10
GCCCCCGACGAGGAGGACCACGTCCTGGTGCTCCATAAGGGCAACTTCGACGAGGCGCTG
AlaProAspGluGluAspHisValLeuValLeuHisLysGlyAsnPheAspGluAlaLeu
1                            10                           20
GCGGCCCACAAGTACCTGCTGGTGGAGTTCTACGCCCCATGGTGCGGCCACTGCAAGGCT
AlaAlaHisLysTyrLeuLeuValGluPheTyrAlaProTrpCysGlyHisCysLysAla
                             30                           40
CTGGCCCCGGAGTATGCCAAAGCAGCTGGGAAGCTGAAGGCAGAAGGTTCTGAGATCAGA
LeuAlaProGluTyrAlaLysAlaAlaGlyLysLeuLysAlaGluGlySerGluIleArg
                             50                           60
CTGGCCAAGGTGGATGCCACTGAAGAGTCTGACCTGGCCCAGCAGTATGGTGTCCGAGGC
LeuAlaLysValAspAlaThrGluGluSerAspLeuAlaGlnGlnTyrGlyValArgGly
                             70                           80
TACCCCACCATCAAGTTCTTCAAGAATGGAGACACAGCTTCCCCCAAAGAGTACACAGCT
TyrProThrIleLysPhePheLysAsnGlyAspThrAlaSerProLysGluTyrThrAla
                             90                          100
GGCCGAGAAGCGGATGATATCGTGAACTGGCTGAAGAAGCGCACGGGCCCCGCTGCCAGC
GlyArgGluAlaAspAspIleValAsnTrpLeuLysLysArgThrGlyProAlaAlaSer
                            110                          120
```

```
ACGCTGTCCGACGGGGCTGCTGCAGAGGCCTTGGTGGAGTCCAGTGAGGTGGCCGTCATT
ThrLeuSerAspGlyAlaAlaAlaGluAlaLeuValGluSerSerGluValAlaValIle
            130                                           140

GGCTTCTTCAAGGACATGGAGTCGGACTCCGCAAAGCAGTTCTTCTTGGCAGCAGAGGTC
GlyPhePheLysAspMetGluSerAspSerAlaLysGlnPheLeuLeuAlaAlaGluVal
            150                                           160

ATTGATGACATCCCCTTCGGGATCACATCTAACAGCGATGTGTTCTCCAAATACCAGCTG
IleAspAspIleProPheGlyIleThrSerAsnSerAspValPheSerLysTyrGlnLeu
            170                                           180

GACAAGGATGGGGTTGTCCTCTTTAAGAAGTTTGACGAAGGCCGGAACAACTTTGAGGGG
AspLysAspGlyValValLeuPheLysLysPheAspGluGlyArgAsnAsnPheGluGly
            190                                           200

GAGGTCACCAAAGAAAAGCTTCTGGACTTCATCAAGCACAACCAGTTGCCCCTGGTCATT
GluValThrLysGluLysLeuLeuAspPheIleLysHisAsnGlnLeuProLeuValIle
            210                                           220

GAGTTCACCGAGCAGACAGCCCCGAAGATCTTCGGAGGGGAAATCAAGACTCACATCCTG
GluPheThrGluGlnThrAlaProLysIlePheGlyGlyGluIleLysThrHisIleLeu
            230                                           240

CTGTTCCTGCCGAAAAGCGTGTCTGACTATGAGGGCAAGCTGAGCAACTTCAAAAAAGCG
LeuPheLeuProLysSerValSerAspTyrGluGlyLysLeuSerAsnPheLysLysAla
            250                                           260

GCTGAGAGCTTCAAGGGCAAGATCCTGTTTATCTTCATCGACAGCGACCACACTGACAAC
AlaGluSerPheLysGlyLysIleLeuPheIlePheIleAspSerAspHisThrAspAsn
            270                                           280

CAGCGCATCCTGGAATTCTTCGGCCTAAAGAAAGAGGAGTGCCCCGGCCGTGCGCCTCATC
GlnArgIleLeuGluPhePheGlyLeuLysLysGluGluCysProAlaValArgLeuIle
            290                                           300

ACGCTGGAGGAGGAGATGACCAAATATAAGCCAGAGTCAGATGAGCTGACGGCAGAGAAG
ThrLeuGluGluGluMetThrLysTyrLysProGluSerAspGluLeuThrAlaGluLys
            310                                           320

ATCACCGAGTTCTGCCACCGCTTCCTGGAGGGCAAGATTAAGCCCCACCTGATGAGCCAG
IleThrGluPheCysHisArgPheLeuGluGlyLysIleLysProHisLeuMetSerGln
            330                                           340

GAGCTGCCTGACGACTGGGACAAGCAGCCTGTCAAAGTGCTGGTTGGGAAGAACTTTGAA
GluLeuProAspAspTrpAspLysGlnProValLysValLeuValGlyLysAsnPheGlu
            350                                           360

GAGGTTGCTTTTGATGAGAAAAAGAACGTCTTTGTAGAGTTCTATGCCCCGTGGTGCGGT
GluValAlaPheAspGluLysLysAsnValPheValGluPheTyrAlaProTrpCysGly
            370                                           380

CACTGCAAGCAGCTGGCCCCCATCTGGGATAAGCTGGGAGAGACGTACAAGGACCACGAG
HisCysLysGlnLeuAlaProIleTrpAspLysLeuGlyGluThrTyrLysAspHisGlu
            390                                           400
```

```
AACATAGTCATCGCCAAGATGGACTCCACGGCCAACGAGGTGGAGGCGGTGAAAGTGCAC
AsnIleValIleAlaLysMetAspSerThrAlaAsnGluValGluAlaValLysValHis
         410                                              420

AGCTTCCCCACGCTCAAGTTCTTCCCCGCCAGCGCCGACAGGACGGTCATCGACTACAAT
SerPheProThrLeuLysPhePheProAlaSerAlaAspArgThrValIleAspTyrAsn
         430                                              440

GGGGAGCGGACACTGGATGGTTTTAAGAAGTTCCTGGAGAGTGGTGGCCAGGATGGGGCC
GlyGluArgThrLeuAspGlyPheLysLysPheLeuGluSerGlyGlyGlnAspGlyAla
         450                                              460

GGAGATGATGACGATCTAGAAGATCTTGAAGAAGCAGAAGAGCCTGATCTGGAGGAAGAT
GlyAspAspAspAspLeuGluAspLeuGluGluAlaGluGluProAspLeuGluGluAsp
         470                                              480

GATGATCAAAAAGCTGTGAAAGATGAACTGTAACACAGAGAGCCAGACCTGGGCACCAAA
AspAspGlnLysAlaValLysAspGluLeu
         490
```

CCCGGACCTCCCAGTGGGCTGCACACCCAGCAGCACAGCCTCCAGACGCCCGCAGACCCT

CCCAGCGAGGGAGCGTCGATTGGAAATGCAGGGAACTTTTCTGAAGCCACACTTCACTCT

ACCACACGTGCAAATCTAAACCCGTCTTCCTTTGCTTTTCAACTTTTGGAAAAGGGTTTA

TTTCCAGGCCAGCCCAGCCCAGCCCATCTTGGTGGGCCTTTTTTTTTAAATCGTGATGTA

CTTTTTTTGTACCTGGTTTTGTCCAGAGTGCTCGCTAAAATGTTTTGGACTCTCACGCTG

GCAATGTCTCTCATTCCTGTTAGGTTTATACTATCACTTTAAAAAAATTCCGTCTGTGGG

ATTTTTAGACATTTTTGGACGTCAGGGTGTGTGCTCCACCTTGGCCAGGCCTCCCTGGGA

CTCCTGCCCTCTGTGGGGCAGAACCAGGCAAGGCTGGACGGGTCCCTCACCTCATGCGGT

ATTGCCATGGTGGAGCGTGGCTCCTGCATCATTTGATTAAATGGAGACTTTCCGGTCTCT

GTCACAGGCCGCTCCCCAACCGTGAGTGGAGGGTGTGGCTGGGCCAGGACAAGCCCAGCA

Fig. 2C (continued)

CTGTGCCAGGCAGAACCGGGACCCTTCGTTTCCAGGCTGGGAGACAGCCAAGGATGCTTG

GCCCCCTCCTTCCCCAAGCCAGGGTCCTTATTGCTCTGTGATGTCCAGGGTGGCCTGAGG

AGCTGAATCACATGTTGACAGTTCTTCAGGCATTTCTACCACAATATTGGAATTGGACAC

ATTGGCCAAATAAAGTTAAAATTTTCTGCCAAAAAAAAAAAA

1
AlaProGluGluGluAspHisValLeuValLeuArgLysSerAsnPheAlaGluAla
LeuAlaAlaHisLysTyrLeuLeuValGluPheTyrAlaProTrpCysGlyHisCysLys
AlaLeuAlaProGluTyrAlaLysAlaAlaGlyLysLeuLysAlaGluGlySerGluIle
ArgLeuAlaLysValAspAlaThrGluGluSerAspLeuAlaGlnGlnTyrGlyValArg
GlyTyrProThrIleLysPhePheArgAsnGlyAspThrAlaSerProLysGluTyrThr
AlaGlyArgGluAlaAspAspIleValAsnTrpLeuLysLysArgThrGlyProAlaAla
ThrThrLeuProAspGlyAlaAlaAlaGluSerLeuValGluSerSerGluValAlaVal
IleGlyPhePheLysAspValGluSerAspSerAlaLysGlnPheLeuGlnAlaAlaGlu
AlaIleAspAspIleProPheGlyIleThrSerAsnSerAspValPheSerLysTyrGln
LeuAspLysAspGlyValValLeuPheLysLysPheAspGluGlyArgAsnAsnPheGlu
GlyGluValThrLysGluAsnLeuLeuAspPheIleLysHisAsnGlnLeuProLeuVal
IleGluPheThrGluGlnThrAlaProLysIlePheGlyGlyGluIleLysThrHisIle
LeuLeuPheLeuProLysSerValSerAspTyrAspGlyLysLeuSerAsnPheLysThr
AlaAlaGluSerPheLysGlyLysIleLeuPheIlePheIleAspSerAspHisThrAsp
AsnGlnArgIleLeuGluPhePheGlyLeuLysLysGluGluCysProAlaValArgLeu
IleThrLeuGluGluGluMetThrLysTyrLysProGluSerGluGluLeuThrAlaGlu
ArgIleThrGluPheCysHisArgPheLeuGluGlyLysIleLysProHisLeuMetSer
GlnGluLeuProGluAspTrpAspLysGlnProValLysValLeuValGlyLysAsnPhe
GluAspValAlaPheAspGluLysLysAsnValPheValGluPheTyrAlaProTrpCys
GlyHisCysLysGlnLeuAlaProIleTrpAspLysLeuGlyGluThrTyrLysAspHis
GluAsnIleValIleAlaLysMetAspSerThrAlaAsnGluValGluAlaValLysVal
HisSerPheProThrLeuLysPhePheProAlaSerAlaAspArgThrValIleAspTyr
AsnGlyGluArgThrLeuAspGlyPheLysLysPheLeuGluSerGlyGlnAspGly
AlaGlyAspAspAspAspLeuGluAspLeuGluGluAlaGluProAspMetGluGlu
AspAspAspGlnLysAlaValLysAspGluLeu

Fig. 3

```
              10           20          30          40          50          60
                                                                          -18
                                                                       MetLeuArg
        GAATTCGGGGCGGCGCCAACCGAAGCGCCCCGCCTGATCCGTGTCCGACATGCTGCGC
                                                                -1  1
ArgAlaLeuLeuCysLeuAlaValAlaAlaLeuValArgAlaAspAlaProGluGluGlu
CGCGCTCTGCTGTGCCTGGCCGTGGCCGCCCTGGTGCGCGCCGACGCCCCCGAGGAGGAG

AspHisValLeuValLeuArgLysSerAsnPheAlaGluAlaLeuAlaAlaHisLysTyr
GACCACGTCCTGGTGCTGCGGAAAAGCAACTTCGCGGAGGCGCTGGCGGCCCACAAGTAC

LeuLeuValGluPheTyrAlaProTrpCysGlyHisCysLysAlaLeuAlaProGluTyr
CTGCTGGTGGAGTTCTATGCCCCTTGGTGTGGCCACTGCAAGGCTCTGGCCCCTGAGTAT

AlaLysAlaAlaGlyLysLeuLysAlaGluGlySerGluIleArgLeuAlaLysValAsp
GCCAAAGCCGCTGGGAAGCTGAAGGCAGAAGGTTCCGAGATCAGGTTGGCCAAGGTGGAC

AlaThrGluGluSerAspLeuAlaGlnGlnTyrGlyValArgGlyTyrProThrIleLys
GCCACGGAGGAGTCTGACCTGGCCCAGCAGTACGGCGTGCGCGGCTATCCCACCATCAAG

PhePheArgAsnGlyAspThrAlaSerProLysGluTyrThrAlaGlyArgGluAlaAsp
TTCTTCAGGAATGGAGACACGGCTTCCCCCAAGGAATATACAGCTGGCAGAGAGGCTGAT

AspIleValAsnTrpLeuLysLysArgThrGlyProAlaAlaThrThrLeuProAspGly
GACATCGTGAACTGGCTGAAGAAGCGCACGGGCCCGGCTGCCACCACCCTGCCTGACGGC

AlaAlaAlaGluSerLeuValGluSerSerGluValAlaValIleGlyPhePheLysAsp
GCAGCTGCAGAGTCCTTGGTGGAGTCCAGCGAGGTGGCTGTCATCGGCTTCTTCAAGGAC

ValGluSerAspSerAlaLysGlnPheLeuGlnAlaAlaGluAlaIleAspAspIlePro
GTGGAGTCGGACTCTGCCAAGCAGTTTTTGCAGGCAGCAGAGGCCATCGATGACATACCA

PheGlyIleThrSerAsnSerAspValPheSerLysTyrGlnLeuAspLysAspGlyVal
TTTGGGATCACTTCCAACAGTGACGTGTTCTCCAAATACCAGCTCGACAAAGATGGGGTT

ValLeuPheLysLysPheAspGluGlyArgAsnAsnPheGluGlyGluValThrLysGlu
GTCCTCTTTAAGAAGTTTGATGAAGGCCGGAACAACTTTGAAGGGGAGGTCACCAAGGAG

AsnLeuLeuAspPheIleLysHisAsnGlnLeuProLeuValIleGluPheThrGluGln
AACCTGCTGGACTTTATCAAACACAACCAGCTGCCCCTTGTCATCGAGTTCACCGAGCAG

ThrAlaProLysIlePheGlyGlyGluIleLysThrHisIleLeuLeuPheLeuProLys
ACAGCCCCGAAGATTTTTGGAGGTGAAATCAAGACTCACATCCTGCTGTTCTTGCCCAAG

SerValSerAspTyrAspGlyLysLeuSerAsnPheLysThrAlaAlaGluSerPheLys
AGTGTGTCTGACTATGACGGCAAACTGAGCAACTTCAAAACAGCAGCCGAGAGCTTCAAG

GlyLysIleLeuPheIlePheIleAspSerAspHisThrAspAsnGlnArgIleLeuGlu
GGCAAGATCCTGTTCATCTTCATCGACAGCGACCACACCGACAACCAGCGCATCCTCGAG

PhePheGlyLeuLysLysGluGluCysProAlaValArgLeuIleThrLeuGluGluGlu
TTCTTTGGCCTGAAGAAGGAAGAGTGCCCGGCCGTGCGCCTCATCACCCTGGAGGAGGAG

MetThrLysTyrLysProGluSerGluGluLeuThrAlaGluArgIleThrGluPheCys
ATGACCAAGTACAAGCCCGAATCGGAGGAGCTGACGGCAGAGAGGATCACAGAGTTCTGC
```

Fig 5A (continued)

```
HisArgPheLeuGluGlyLysIleLysProHisLeuMetSerGlnGluLeuProGluAsp
CACCGCTTCCTGGAGGGCAAAATCAAGCCCCACCTGATGAGCCAGGAGCTGCCGGAGGAC

TrpAspLysGlnProValLysValLeuValGlyLysAsnPheGluAspValAlaPheAsp
TGGGACAAGCAGCCTGTCAAGGTGCTTGTTGGGAAGAACTTTGAAGACGTGGCTTTTGAT

GluLysLysAsnValPheValGluPheTyrAlaProTrpCysGlyHisCysLysGlnLeu
GAGAAAAAAAACGTCTTTGTGGAGTTCTATGCCCCATGGTGTGGTCACTGCAAACAGTTG

AlaProIleTrpAspLysLeuGlyGluThrTyrLysAspHisGluAsnIleValIleAla
GCTCCCATTTGGGATAAACTGGGAGAGACGTACAAGGACCATGAGAACATCGTCATCGCC

LysMetAspSerThrAlaAsnGluValGluAlaValLysValHisSerPheProThrLeu
AAGATGGACTCGACTGCCAACGAGGTGGAGGCCGTCAAAGTGCACAGCTTCCCCACACTC

LysPhePheProAlaSerAlaAspArgThrValIleAspTyrAsnGlyGluArgThrLeu
AAGTTCTTTCCTGCCAGTGCCGACAGGACGGTCATTGATTACAACGGGGAACGCACGCTG

AspGlyPheLysLysPheLeuGluSerGlyGlyGlnAspGlyAlaGlyAspAspAspAsp
GATGGTTTTAAGAAATTCCTGGAGAGCGGTGGCCAGGATGGGGCAGGGGATGATGACGAT

LeuGluAspLeuGluGluAlaGluGluProAspMetGluGluAspAspAspGlnLysAla
CTCGAGGACCTGGAAGAAGCAGAGGAGCCAGACATGGAGGAAGACGATGATCAGAAAGCT
                                                      490
ValLysAspGluLeutrm
GTGAAAGATGAACTGTAATACGCAAAGCCAGACCCGGGCGCTGCCGAGACCCCTCGGGGG

CTGCACACCCAGCAGCAGCGCACGCCTCCGAAGCCTGCGGCCTCGCTTGAAGGAGGGCGT

CGCCGGAAACCCAGGGAACCTCTCTGAAGTGACACCTCACCCCTACACACCGTCCGTTCA

CCCCCGTCTCTTCCTTCTGCTTTTCGGTTTTTGGAAAGGGATCCATCTCCAGGCAGCCCA

CCCTGGTGGGGCTTGTTTCCTGAAACCATGATGTACTTTTTCATACATGAGTCTGTCCAG

AGTGCTTGCTACCGTGTTCGGAGTCTCGCTGCCTCCCTCCCGCGGGAGGTTTCTCCTCTT

TTTGAAAATTCCGTCTGTGGGATTTTTAGACATTTTTCGACATCAGGGTATTTGTTCCAC

CTTGGCCAGGCCTCCTCGGAGAAGCTTGTCCCCCGTGTGGGAGGGACGGAGCCGGACTGG

ACATGGTCACTCAGTACCGCCTGCAGTGTCGCCATGACTGATCATGGCTCTTGCATTTTT

GGGTAAATGGAGACTTCCGGATCCTGTCAGGGTGTCCCCCATGCCTGGAAGAGGAGCTGG

TGGCTGCCAGCCCTGGGGCCCGGCACAGGCCTGGGCCTTCCCCTTCCCTCAAGCCAGGGC

TCCTCCTCCTGTCGTGGGCTCATTGTGACCACTGGCCTCTCTACAGCACGGCCTGTGGCC

TGTTCAAGGCAGAACCACGACCCTTGACTCCCGGGTGGGGAGGTGGCCAAGGATGCTGGA

GCTGAATCAGACGCTGACAGTTCTTCAGGCATTTCTATTTCACAATCGAATTGAACACAT

TGGCCAAATAAAGTTGAAATTTTACCACCAAAAAAAAAAAAAAAA
```

Fig. 5B

Fig. 8
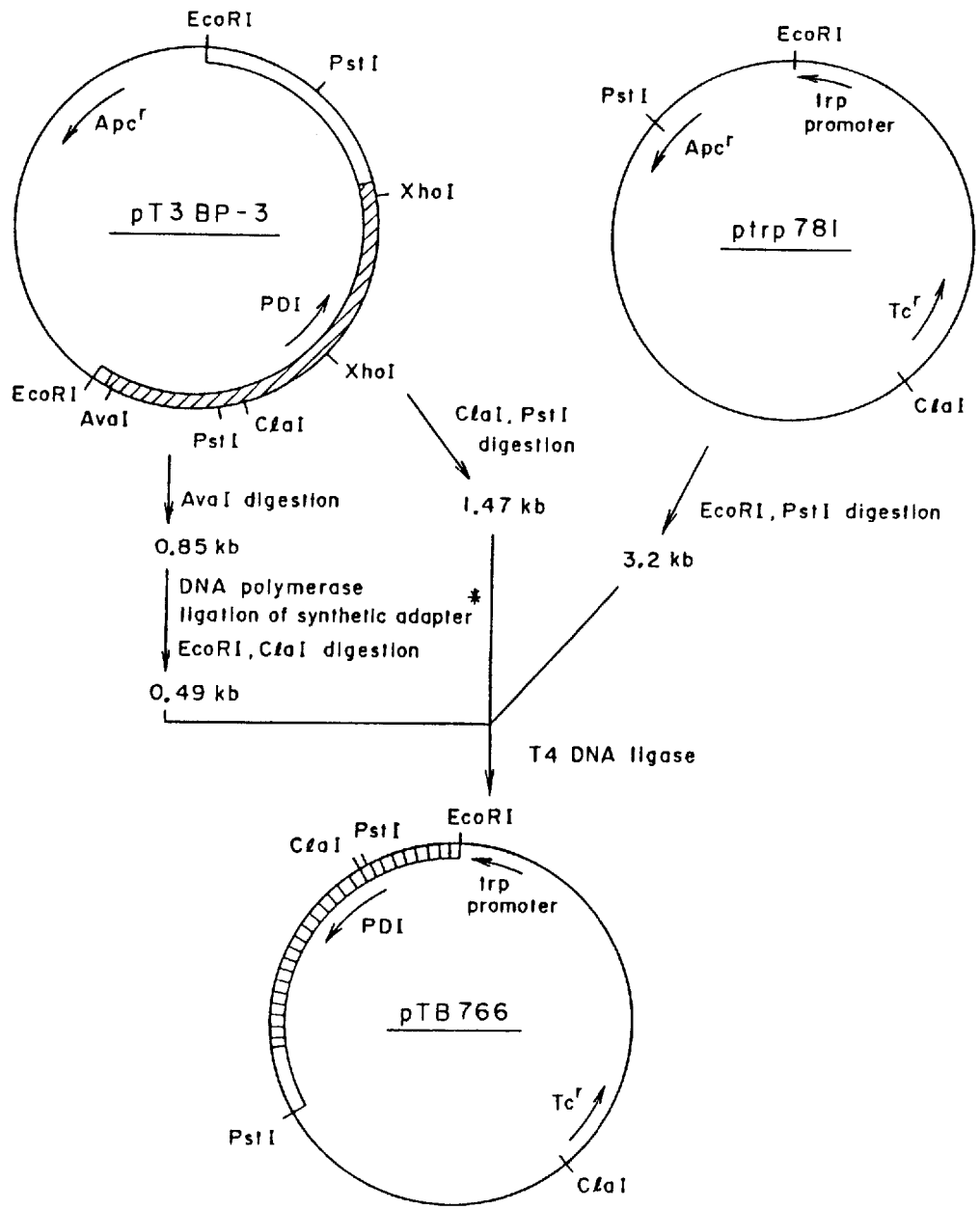
* synthetic adapter

PROTEIN DISULFIDE ISOMERASE AND METHOD OF USING

This is a continuation of application Ser. No. 07/982,138, filed on Nov. 25, 1992, now U.S. Pat. No. 5,700,678, which is a continuation of U.S. Ser. No. 07/635,812, filed Jan. 2, 1991, now abandoned, which is a continuation of U.S. Ser. No. 07/199,307, filed May 26, 1988, now abandoned.

FIELD OF INDUSTRIAL APPLICATION

The present invention relates to a polypeptide and a method for producing the polypeptide, and specifically relates to a polypeptide possessing protein disulfide isomerase activity and a method for producing the polypeptide.

BRIEF DESCRIPTION OF THE DRAWINGS

In FIG. 1, (1) represents the cDNA as cloned in pT3BP-1 and (2) represents the cDNA as cloned in pT3BP-2. The abbreviations A, E, H, P and S represent Aat II, EcoR I, Hinc II, Pvu II and Ssp I, respectively; ■ represents the portion corresponding to the amino acid sequence derived from tryptic peptide mapping for purified T3BP protein.

FIGS. 2A, 2B, 2C and 2D shows the base sequence of the cDNA as cloned in the pT3BP-2 obtained in Reference Example 2 and the amino acid sequence deduced from the base sequence.

FIG. 3 shows the amino acid sequence of human PDI.

FIG. 4 shows a schematized cleavage map of the cDNA with restriction enzymes as cloned in pT3BP-3 obtained in Example 1. In FIG. 4, the abbreviations B, C, E, H and P represent BamH I, Cla I, EcoR I, Hind III and Pst I, respectively.

FIGS. 5A and 5B shows the base sequence of the cDNA as cloned in pT3BP-3 obtained in Example 1 and the amino acid sequence deduced from the base sequence.

In FIG. 7A, represents a fluorescent photomicrograph showing the morphology of the PDI gene-introduced cell and FIG. 7(B) represents a fluorescent photomicrograph of the morphology of the cell without the gene introduction as the control.

FIG. 8 shows the construction scheme for the plasmid for expression of the human PDI gene in *Escherichia coli*.

In FIG. 9, the lanes B and D correspond to DH1/pTB766 and MM294/pTB766, respectively; the lanes A and C correspond to DH1/ptrp781 and MM294/ptrp781, respectively.

PRIOR ART AND PROBLEMS TO BE SOLVED

Figure 1:
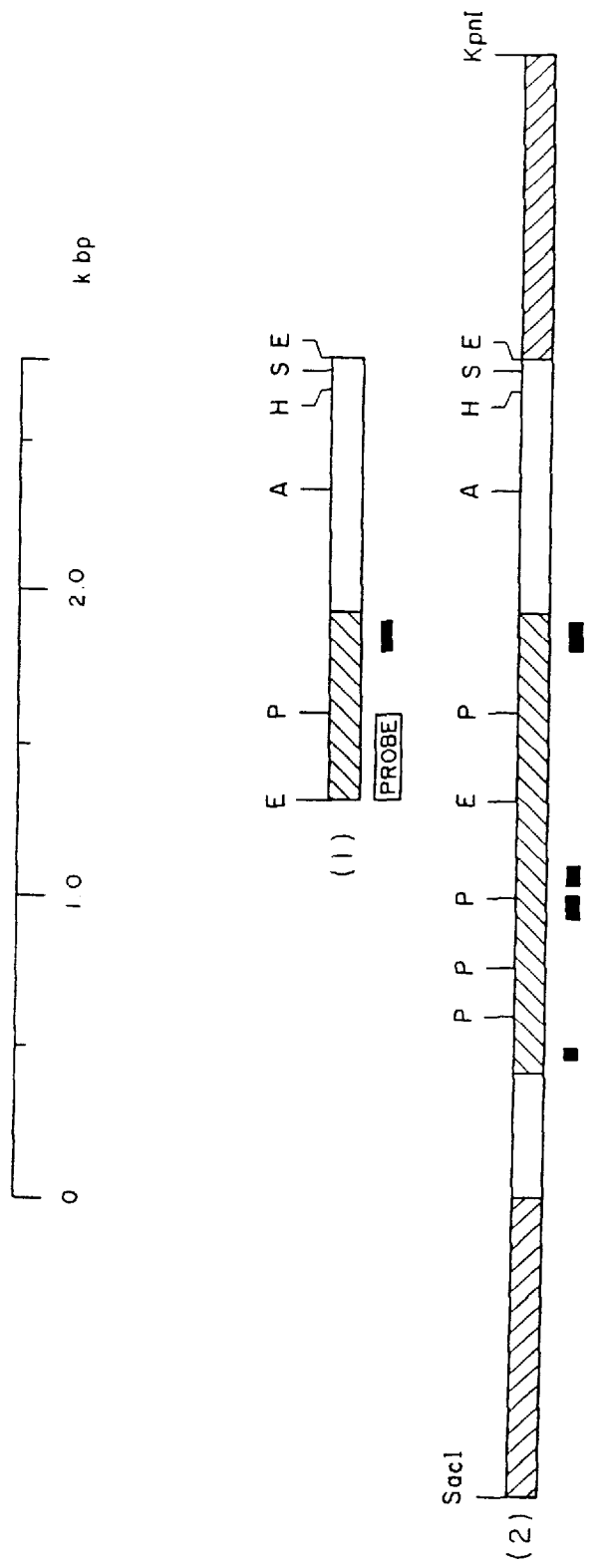
FIG. 1 shows schematized cleavage maps of the cDNA with restriction enzymes as cloned in pT3BP-1 and pT3BP-2 obtained in Reference Example 2.

It is generally known that formation of disulfide bonds is extremely important in the retention of protein's configuration and the expression of its activity. In eukaryotic cells, disulfide bonds are formed in endoplasmic reticula simultaneously with or immediately after protein translation [J. Biol. Chem., 257, 8847 (1982)]. Such disulfide bonds can also be non-enzymatically formed in vitro; however, the reaction rate is lower than that in vivo, but also the conditions in vitro do not reflect those in vivo. Based on this fact, Anfinsen et al. conjectured that a protein named as disulfide interchange protein would function in the formation of disulfide bonds in vivo [J. Biol. Chem., 238, 628 (1963)]. Although this conjecture still remains a hypothesis, enzymes which act on reduced and scrambled ribonucleases (both are inactive types) to promote the formation of true disulfide bonds for active ribonucleases, were discovered in various eukaryotes and purified [Biochemistry, 20, 6594 (1981); Biochem. J., 213, 225 (1983); Biochem. J., 213, 245 (1983)]. The scrambled ribonuclease, which is prepared by reduction and re-oxidization under denaturing conditions, is a mixture of various molecular species formed as a result of random recombination of the 4 pairs of disulfide bonds in the active ribonuclease [Biochem. J., 213, 235 (1983)]. The enzyme which converts an inactive ribonuclease to an active ribonuclease, is named protein disulfide isomerase (PDI, EC 5.3.4.1), and is a dimer comprising 2 identical subunits of a molecular weight of 52,000 to 62,000, its isoelectric point being 4.0 to 4.5 [Trends in Biochem. Sci., 9, 438 (1984); Methods in Enzymol., 107, 281 (1984)]. The already-known protein disulfide reductase (also called glutathione insulin transhydrogenase, EC 1.8.4.2.) is thought of as identical with PDI [Eur. J. Biochem., 32, 27 (1973); Biochemistry, 14, 2115 (1975)].

In 1985 Edman et al. succeeded in cloning a complementary DNA of rat liver PDI and determined its entire base sequence [Nature, 317, 267 (1985)]. Rat liver PDI comprises 489 amino acids with a signal peptide consisting of 19 amino acids being added to its amino terminal. It also has regions homologous with *Escherichia coli* thioredoxin [Eur. J. Biochem., 6, 475 (1968); Proc. Natl. Acad. Sci. USA, 72, 2305 (1975); Methods in Enzymol., 107, 295 (1984)], which is known as a cofactor for various oxidation-reduction reactions such as ribonucleotide reductase reaction, in two sites, namely in the vicinities of the amino terminal and carboxyl terminal. Each region includes a homologous sequence having 2 Cys (Trp-Cys-Gly-Cys-Lys), which is considered to catalyze PDI reaction via exchange between disulfide and sulfhydryl. It has also recently been reported that *Escherichia coli* thioredoxin exhibits PDI activities in the presence of reduced or scrambled ribonuclease as the substrate [Proc. Natl. Acad. Sci. USA, 83, 7643 (1986)].

The utility of PDI may include its application to refolding of recombinant proteins produced by *Escherichia coli*. Due to recent rapid progress in genetic engineering technology, mass production of eukaryotic proteins using *Escherichia coli* has become possible; however, the recombinant proteins thus obtained may lack true disulfide bonds, or may have misformed disulfide bonds [EMBO Journal, 4, 775 (1985); in Genetic Engineering, Vol. 4 (edited by Williamson, R.), pp. 127 (1983)]. A refolding procedure is therefore required to obtain an active recombinant protein having true disulfide bonds. This procedure has been chemically performed by oxidation-reduction reaction using a redox buffer, etc.; however, it appears that the use of PDI, which may function in vivo, is more advantageous in specific formation of true disulfide bonds. The use of PDI is considered to be extremely efficient specifically for recombinant proteins having a large number of disulfide bonds. It is also possible to introduce the PDI-encoding gene into a transformed *Escherichia coli* for the reaction with the recombinant protein in the *Escherichia coli* cell.

In accordance with the conventional production method for PDI, it is difficult to obtain the starting material, but also the amount of obtainable PDI is limited; therefore, it is desired that a technology enabling mass production of highly purified PDI will be developed. In rats and bovines, the PDI genes have already been cloned [Nature, 317, 267 (1985)]; however, no case of obtaining purified active PDI by the expression of the PDI gene in *Escherichia coli*, etc. has been reported so far. Also, no case of the cloning of PDI of an eukaryote other than the above-mentioned eukaryotes has been known up to now.

The present inventors have made studies on the biological actions, proteochemical properties, etc. of the protein (T3 binding protein, hereinafter abbreviated T3BP) which binds specifically with the thyroid hormone T3 (3,3',5-triiodothyronine, hereinafter abbreviated T3). T3BP is known to be present in cell membranes and cytoplasm of mammalian cells, and the T3 receptor is known to be present in cell nuclei. Some of the present inventors succeeded in preparing an antibody against purified T3BP as obtained from bovine liver cell membranes [Horiuchi, R. and Yamauchi, K.: in Gunma Symposia on Endocrinology, 23 (Center for Academic Publication Japan, Tokyo: VNU Science Press, BV. Utrecht), pp. 149–166 (1986)], and have endeavored to clone the gene which encodes T3BP protein by means of various genetic engineering techniques, thus finding that the bovine liver T3BP's cDNA obtained using the above anti-T3BP antibody as the probe is encoding bovine PDI protein [International Application Number: PCT/JP87/00058; filing date of the international application: Jan. 28, 1987].

In general, the proteins of animals which are more closely related to humans have extremely high homology in amino acid sequences with the human proteins; even most of the portions of different amino acids are derived by one-point mutation of the codons. It is therefore inferred that the DNA sequence of the above-mentioned bovine T3BP (PDI) gene extremely resembles the DNA sequence of the human PDI gene. The present inventors then found that human PDI is produced by cloning from human cells the human PDI gene using a part of the bovine PDI gene as the DNA probe, constructing a recombinant DNA containing said human PDI gene, and cultivating the transformant which has resulted from transformation with said DNA. The present inventors have made further investigations based on these findings to complete this invention.

MEANS OF SOLVING THE PROBLEMS

The present invention provides (1) a recombinant DNA containing the base sequence (I) which encodes the amino acid sequence of FIG. 3, (2) a transformant which has resulted from transformation with a vector carrying the base sequence (I), (3) a polypeptide containing the amino acid sequence of FIG. 3 [hereinafter abbreviated human PDI or human PDI (II)], and (4) a method for producing human PDI characterized in that a transformant which has resulted from transformation with a vector carrying the base sequence (I) is cultivated to allow the transformant to produce and accumulate in the culture human PDI, which is then recovered.

The base sequence (I) may be any base sequence, as long as it encodes the amino acid sequence of FIG. 3, but it is preferable that the base sequence be the base sequence from 104 (the 1st base G of the codon which encodes the +1 amino acid Ala) to 1573 (the 3rd base G of the codon which encodes the +490 amino acid Leu) as presented on the lower line of FIG. 5. Also preferred is the base sequence from 104 to 1573 as presented on the lower line of FIG. 5 with a translational start codon ATG or the base sequence from 50 ( the 1st base A of the codon which encodes the amino acid −18 Met) to 103 (the 3rd base C of the codon which encodes the amino acid −1 Asp) added thereto at a site upstream from its 5' end. Preferred examples also include the base sequence from 104 to 1573 as presented on the lower line of FIG. 5 with GAC or ATGGAC added thereto at a site upstream from its 5' end, the base sequence from 107 to 1573 as presented on the lower line of FIG. 5, and the base sequence from 107 to 1573 as presented on the lower line of FIG. 5 with ATG added thereto at a site upstream from its 5' end.

Examples of the human PDI (II) include the polypeptide represented by the amino acid sequence of FIG. 3, the polypeptide represented by the amino acid sequence of FIG. 3 with Met or the peptide represented by the amino acid sequence from −18 to −1 as presented on the upper line of FIG. 5 added thereto at its N-terminal, the polypeptide represented by the amino acid sequence of FIG. 3 with Asp or Met-Asp added thereto at its N-terminal, the polypeptide represented by the amino acid sequence of FIG. 5 with the amino acid +1 Ala as presented on an upper line of FIG. 5 eliminated therefrom, and the polypeptide represented by the amino acid sequence of FIG. 5 with the amino acid +1 Ala as presented on an upper line of FIG. 5 replaced by Met. These peptides may be sugar-linked glycoproteins, and may also be fused proteins with other polypeptides.

An expression vector carrying the base sequence which encodes the human PDI polypeptide for the present invention can, for example, be produced by (i) separating a mRNA which encodes human PDI, (ii) synthesizing from said RNA a single-stranded complementary DNA (cDNA) and then a double-stranded DNA, (iii) inserting said complementary DNA in a phage or plasmid, (iv) using the obtained recombinant phage or plasmid to transform the host, (v) cultivating the obtained transformant, and then isolating the phage or plasmid carrying the desired DNA from the transformant by an appropriate method such as immunoassay using the anti-T3BP antibody, or plaque hybridization or colony hybridization using a radiolabeled probe, (vi) cleaving the desired cloned DNA from the phage or plasmid, and (vii) ligating said cloned DNA to the downstream of a promoter in a vehicle.

The mRNA for encoding human PDI can be obtained from various human PDI-producing cells, such as human liver cells and placenta cells.

The methods of preparing RNA from human PDI-producing cells include the guanidine thiocyanate method [Chirgwin, J. M. et al.: Biochemistry, 18, 5294 (1979)].

Using the RNA thus obtained as the template and reverse transcriptase, the cDNA is synthesized in accordance with, for example, the method of Okayama, H. et al. [Mol. Cell. Biol., 2, 161 (1982) and ibid, 3, 280 (1983)] or the method of Gubler, U. and Hoffman, B. J. [Gene, 25, 263 (1983)], and the cDNA thus obtained is inserted in the plasmid or phage.

As examples of plasmids to which the cDNA is inserted, there are mentioned *Escherichia coli*-derived plasmids pBR322 [Gene, 2, 95 (1977)], pBR325 [Gene, 4, 121 (1978)], pUC12 [Gene, 19, 259 (1982)], and pUC13 [Gene, 19, 259 (1982)], and *Bacillus subtilis*-derived plasmid pUB110 [Biochem. Biophys. Res. Commun., 112, 678 (1983)], but any other plasmid can also be used, as long as it is replicated and carried by the host. As examples of phage vectors to which the cDNA is inserted, there is mentioned λgt11 [Young, R., and Davis, R., Proc. Natl. Acad. Sci. USA, 80, 1194 (1983)], but any other phage vector can be used, as long as it is capable of proliferating in the host.

The methods of inserting the cDNA into the plasmid include the method described in Maniatis, T. et al., "Molecular Cloning", Cold Spring Harbor Laboratory, p. 239 (1982). The methods of inserting the cDNA into the phage vector include the method of Hyunh, T. V. et al. [DNA Cloning, A Practical Approach, 1, 49 (1985)]. The plasmid or phage vector thus obtained is then introduced into an appropriate host such as *Escherichia coli* or *Bacillus subtilis*.

Examples of such *Escherichia coli* include *Escherichia coli* K12 DH1 [Proc. Natl. Acad. Sci. USA, 60, 160 (1968)], JM103 [Nucl. Acids Res., 9, 309 (1981)], JA221 [J. Mol. Biol., 120, 517 (1978)], HB101 [J. Mol. Biol., 41, 459 (1969)], and C600 [Genetics, 39, 440 (1954)].

Examples of such *Bacillus subtilis* include *Bacillus subtilis* MI 114 [Gene, 24, 255 (1983)] and 207–21 [J. Biochem., 95, 87 (1984)].

The methods of transforming the host with the plasmid include the calcium chloride method and calcium chloride/rubidium chloride method described in Maniatis, T. et al., "Molecular Cloning", Cold Spring Harbor Laboratory, p. 249 (1982). Also, the phage vector can, for example, be introduced into grown *Escherichia coli* by means of the in vitro packaging method.

From the transformants thus obtained, the desired clone is selected by well-known methods such as the colony hybridization method [Gene, 10, 63 (1980)], the plaque hybridization method [Science, 196, 180 (1977)], and the DNA base sequence determination method [Proc. Natl. Acad. Sci. USA, 74, 560 (1977); Nucl. Acids Res., 9, 309 (1981)].

Thus, the microorganism carrying the vector having the cloned DNA containing the base sequence which encodes human PDI is obtained.

Figures 2D, 4:
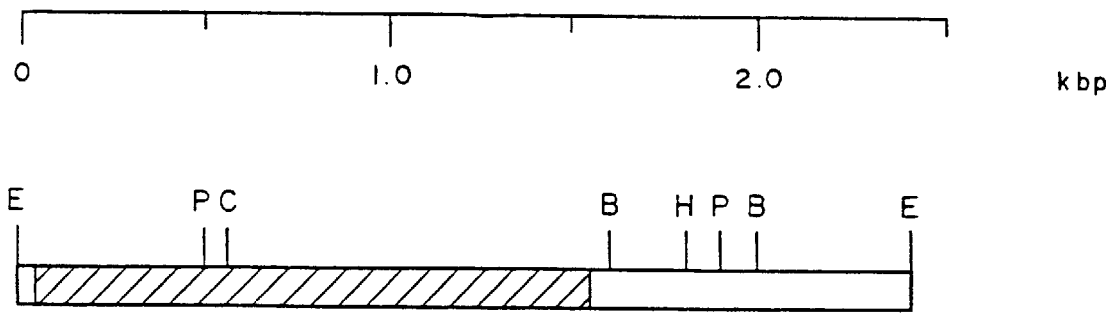

The plasmid pT3BP-3 carried by *Escherichia coli* K12 DH5α/pT3BP-3 as obtained in Example 1 below has a DNA containing a base sequence which encodes human PDI. FIG. 4 shows cleavage sites of said DNA with restriction enzymes. As shown in FIG. 4, said DNA has a total length of about 2.4 Kbp, and is cut into fragments by the restriction enzymes BamH I, EcoR I, Cla I, Hind III, and Pst I.

The plasmid or phage vector is then isolated from the microorganism.

The methods of said isolation include the alkaline extraction method [Birmboim. H. C. et al.: Nucl. Acids Res., 1, 1513 (1979)].

The above-mentioned plasmid or phage vector carrying the cloned DNA containing the base sequence which encodes human PDI may be used as it is, or may be used after digestion with restriction enzymes when necessary.

The cloned gene may be ligated to a site downstream from a promoter in a suitable vehicle (vector) for expression to thereby give the expression vector.

The vectors include the above-mentioned *Escherichia coli*-derived plasmids (e.g. pBR322, pBR325, pUC12, pUC13, ptrp781), *Bacillus subtilis*-derived plasmids (e.g. pUB110, pTM5, pC194), yeast-derived plasmids (e.g. pSH19, pSH15, pGLD906, pGLD906-1, pCDX, pKSV-10), bacteriophages such as λ phage, and animal viruses such as retroviruses and vaccinia viruses.

Said gene may have ATG as the translational start codon at its 5' end, and may also have TAA, TGA, or TAG as the translational termination codon at its 3' end. For expression of said gene, a promoter is connected thereto at a site upstream from said gene. The promoter to be used in this invention may be any promoter that is appropriate and adapted for the host employed for the expression of said gene.

When the host to be transformed is *Escherichia coli*, the trp promoter, lac promoter, rec promoter, $\lambda P_L$ promoter, lpp promoter, etc. are preferred. When the host is *Bacillus subtilis*, the SP01 promoter, SP02 promoter, penP promoter, for instance, are preferred. When the host is yeast, the PHO5 promoter, PGK promoter, GAP (GLD) promoter, ADH promoter, etc. are preferred. In particular, it is preferable that the host is *Escherichia coli* and that the promoter is the trp promoter or $\lambda P_L$ promoter.

When the host is an animal cell, SV40-derived promoters and retrovirus promoters are usable among others. In particular, SV40-derived promoters are preferable.

The thus-constructed vector carrying the DNA containing the base sequence (I) is used to produce transformants.

Examples of the host include prokaryotes such as *Escherichia coli*, *Bacillus subtilis* and actynomycetes, and eukaryotes such as yeasts, fungi and animal cells.

Representative examples of the strains of *Escherichia coli* and *Bacillus subtilis* are the same as those mentioned hereinbefore.

Representative examples of the yeasts include *Saccharomyces cerevisiae* AH22, AH22R⁻, NA87-11A and DKD-5D.

Representative examples of the animal cells include simian COS-7 and Vero cells, Chinese hamster CHO cells and mouse L cells.

The transformation of said *Escherichia coli* is conducted by the method described in Proc. Natl. Acad. Sci. USA, 69, 2110 (1972) or in Gene, 17, 107 (1982), for instance.

The transformation of *Bacillus subtilis* is conducted by the method described in Molec. Gen. Genet., 168, 111 (1979), for instance.

The transformation of yeast is conducted by the method described in Proc. Natl. Acad. Sci. USA, 75, 1929 (1978), for instance.

The transformation of animal cells is conducted by the method described in Virology, 52, 456 (1973), for instance.

In this manner, transformants as transformed with vectors carrying the base sequence (I) are obtained.

In cultivating the transformant obtained by transformation of *Escherichia coli*, *Bacillus subtilis*, an actynomycete, yeast or fungus as the host, a liquid medium is suitable for the cultivation, and the medium contains substances required for the growth of said transformants, for example carbon sources, nitrogen sources and inorganic nutrients. Glucose, dextrin, soluble starch and sucrose, for instance, may serve as carbon sources. The nitrogen sources may include organic or inorganic substances such as ammonium salts, nitrate salts, corn steep liquor, peptone, casein, meat extract, soybean cake and potato extract. The inorganic nutrients may include calcium chloride, sodium dihydrogen phosphate and magnesium chloride.

The medium preferably has a pH of about 5 to 8.

When the host is *Escherichia coli*, M9 medium containing glucose and casamino acids (Miller: J. Exp. Mol. Genet., p. 431, Cold Spring Harbor Laboratory, N.Y., 1972), for instance, is a preferable medium for use. The cultivation is normally carried out at about 14° to 43° C. for about 3 to 24 hours, and aeration and/or stirring may be conducted when necessary.

When the host is *Bacillus subtilis*, the cultivation is normally carried out at about 30° to 40° C. for about 6 to 24 hours, and aeration and/or stirring may be conducted when necessary.

When a transformant obtained from yeast as the host is cultivated, Burkholder's minimum medium [Bostian, K. L. et al.: Proc. Natl. Acad. Sci. USA, 77, 4505 (1980)] and its modified low-Pi medium [Biochem. Biophys. Res. Commun., 138, 268 (1986)], for instance, may be used as the medium. The pH of the medium is preferably adjusted to about 5 to 8. The cultivation is normally carried out at about 20° to 35° C. for about 24 to 72 hours, with aeration and/or stirring when necessary.

As the medium to be used in cultivating a transformant obtained from an animal cell as the host, there are mentioned, for example, MEM medium [Science, 122, 501 (1952)], DMEM medium [Virology, 8, 396 (1959)], RPMI 1640 medium [J. Am. Med. Assoc., 199, 519 (1967)] and 199 medium [Proc. Soc. Exp. Biol. Med., 73, 1 (1950)], which further contain about 5 to 20% fetal calf serum. The medium preferably has a pH of about 6 to 8. The cultivation is normally carried out at about 30° to 40° C. for about 15 to 60 hours, with aeration and/or stirring when necessary.

The human PDI protein of this invention is intracellularly or extracellularly produced and accumulated. For extracting intracellular PDI from the culture, there can be used as appropriate methods such as a method comprising collecting the cells by a known method after cultivation and suspending the cells in a buffer containing a protein denaturant such as guanidine hydrochloride or urea or a surfactant such as Triton-100, followed by centrifugation to thereby give a supernatant containing the human PDI, or a method comprising disrupting the cells by glass beads, by treatment with ultrasonication, by treatment with an enzyme such as lysozyme or by the freeze-thawing method, followed by centrifugation to thereby give a supernatant containing the human PDI.

For separating and purifying the human PDI from the supernatant or the extracellularly produced and accumulated human PDI, well-known methods of separation and purification may be used in appropriate combination. Examples of the known methods of separation and purification include methods based on differences in solubility such as salting-out and solvent precipitation; methods based mainly on differences in molecular weight such as dialysis, ultrafiltration, gel filtration and SDS-polyacrylamide gel electrophoresis; methods based on differences in charge such as ion exchange chromatography; methods based on specific affinity such as affinity chromatography; methods bases on differences in hydrophobicity such as reverse phase high performance liquid chromatography; methods based on differences in isoelectric point such as isoelectric electrophoresis; and methods based on specific adsorption such as hydroxyapatite chromatography. Specifically, ion exchange chromatography with diethylaminoethyl (DEAE) cellulose, DEAE Toyopearl, carboxymethyl (CM) cellulose or CM Toyopearl is efficient for the purification of human PDI protein because said protein is thought of as an acidic protein.

The activity of the human PDI protein obtained as above (PDI activity) can be determined by measuring the rate of conversion of reduced and scrambled ribonucleases as the substrate to active ribonucleases [Biochem. J., 159, 377 (1976); Proc. Natl. Acad. Sci. USA, 83, 7643 (1986); Methods in Enzymology, 107, 281 (1984); J. Biol. Chem., 234, 1512 (1959)].

ACTION AND EFFECT

The human PDI protein of the present invention catalyzes the exchange reaction between sulfhydryl and disulfide in any desired protein for formation of the most stable natural type disulfide bonds. More specifically, said protein, in the presence of dissolved oxygen, an oxidized glutathione (GSSG)-reduced glutathione (GSH) mixture or a reducing agent such as dithiothreitol (DTT), 2-mercaptoethanol or ascorbic acid, acts on a reduced protein to catalyze a reaction by which natural type disulfide bonds are formed, or acts on an oxidized protein having disulfide bonds, specifically non-natural type disulfide bonds to catalyze a reaction by which natural type disulfide bonds are re-formed.

Therefore, in producing a protein having disulfide bonds in its molecules by means of genetic recombination technology, specifically when the host with a recombinant DNA is a cell of a prokaryote such as *Escherichia coli*, *Bacillus subtilis*, or *Bacillus brevis*, human PDI protein can be used to efficiently form natural type disulfide bonds in the relevant protein molecule. Such proteins include cytokines such as interferon-α, interferon-β, interferon-γ, interleukin-1, interleukin-2, B-cell growth factor (BGF), B-cell differentiating factor (BDF), macrophage activating factor (MAF), lymphotoxin (LT), and tumor necrosis factor (TNF); peptide protein hormones such as transforming growth factor (TGF), erythropoietin, epithelial cell growth factor (EGF), fibroblast growth factor (FGF), insulin, and human growth hormone; pathogenic microbial antigen proteins such as hepatitis B virus antigens; enzymes such as peptidase and lysozyme; and blood protein components such as human serum albumin and immunoglobulin.

Said PDI protein used for this purpose may be a purified one, or may be a partially purified one; the purpose can be accomplished simply by allowing said PDI protein to act directly on the above-mentioned intracellularly or extracellularly produced and accumulated desired protein or a purified standard sample thereof. It is also possible to conduct the reaction using a transformant which has been double infected with a recombinant DNA which encodes one of the above-mentioned desired proteins and the recombinant DNA which encodes said PDI protein.

The symbols used in the specification and drawings have the meanings as mentioned in Table 1.

TABLE 1

| | |
|---|---|
| PBS | Phosphate buffered saline |
| DNA | Deoxyribonucleic acid |
| cDNA | Complementary deoxyribonucleic acid |
| A | Adenine |
| T | Thymine |
| G | Guanine |
| C | Cytosine |
| RNA | Ribonucleic acid |
| mRNA | Messenger RNA |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| EDTA | Ethylenediamine tetraacetic acid |
| SDS | Sodium dodecyl sulfate |
| Gly | Glycine |
| Ala | Alanine |

TABLE 1-continued

| | |
|---|---|
| Val | Valine |
| Leu | Leucine |
| Ile | Isoleucine |
| Ser | Serine |
| Thr | Threonine |
| Cys | Cysteine |
| Met | Methionine |
| Glu | Glutamic acid |
| Asp | Aspartic acid |
| Lys | Lysine |
| Arg | Arginine |
| His | Histidine |
| Phe | Phenylalanine |
| Tyr | Tyrosine |
| Trp | Tryptophan |
| Pro | Proline |
| Asn | Asparagine |
| Gln | Glutamine |

The amino acid sequence of the PDI protein of this invention may be partially (up to about 5%) modified (including addition, elimination, and substitution by other amino acids).

EXAMPLES

The present invention will now be described in more detail by means of the following reference examples and working examples, which are not to be construed as limitations on the invention.

Reference Example 1

(Preparation of Bovine Liver mRNA-derived cDNA Library)

The RNAs were extracted from a bovine liver by the guanidine isothiocyanate method [Chirgwin, J. M. et al.: Biochemistry, 18, 5294 (1979)]. From these RNAs, poly (A) RNA was purified by oligo dT cellulose column chromatography [Aviv and Leder: Proc. Natl. Acad. Sci. USA, 69, 1408 (1972)].

Using this poly (A) RNA as the template, the cDNA was prepared by the method of Gubler, U. and Hoffman, B. J. [Gene, 25, 263 (1983)]; then, an EcoR I liner was added to the above cDNA by the method of Huynh, T. V. et al. [DNA cloning I, a practical approach, 1, 49 (1985)], and the cDNA was cloned to the EcoR I site in λgt11 to thereby prepare a cDNA library.

Reference Example 2

(Isolation of Plasmid Containing Bovine PDI cDNA and Determination of its Base Sequence)

Escherichia coli Y1096, after being infected with the cDNA library of λgt11 obtained in Reference Example 1, was spread on an L-broth soft agar plate. Upon the appearance of plaques, a nitrocellulose filter containing IPTG (isopropylthiogalactoside) was placed on the plate, and incubation was conducted for 3 hours. The nitrocellulose filter was then separated and washed with TBS buffer (50 mM Tris, pH 7.9, 150 mM NaCl), after which it was dipped in a 3% gelatin solution.

The nitrocellulose filter thus treated was immersed in a solution of antibodies against T3 binding protein (anti-$BLT_3R$) [Horiuchi, R. and Yamauchi, K.: Gunma Symposia on Endocrinology, 23, P. 149 (1986)] for antigen-antibody reaction. Said filter was then washed with distilled water and TBS buffer, and then reacted with the secondary antibody to select the coloring positive clone λgt11 T3BP-1. The cDNA in the λgt11 T3BP-1 was cleaved with EcoR I and re-cloned to the EcoR I site in the plasmid pUC19 [Gene, 33, 103 (1985)] to thereby prepare the plasmid pT3BP-1. Using the fragment cleaved with the restriction enzymes EcoR I and Pvu II from the cDNA region contained in said plasmid as the DNA probe, $5 \times 10^5$ clones of the cDNA library described in Example 1 were re-screened to thereby select the positive clones.

From one of the clones thus obtained, namely λgt11 T3BP-2, the cDNA was cleaved with Sac I-Kpn I and re-cloned to the Sac I-Kpn I site in the plasmid pUC19 to thereby prepare the plasmid pT3BP-2. (The EcoR I recognition site in the 5' terminal side of the cDNA cloned to λgt11 T3BP-2 had been destroyed.)

E. coli K12 DH5α was transformed with the plasmid pT3BP-2; from the resulting transformant E. coli K12 DH5α/pT3BP-2, the plasmid pT3BP-2 was extracted and purified by the alkali method [Birnboim, H. C. and Doly, J.: Nucl. Acids Res., 11, 1513 (1979)]. The cDNA region contained in this plasmid has a total length of about 2.8 Kbp. FIG. 1 shows a schematized cleavage map of the cDNA region with restriction enzymes.

The base sequence of this cDNA region was determined by the dideoxy-nucleotide chain termination method [Messing, J. et al.: Nucl. Acids Res., 9, 309 (1981)]. FIG. 2 shows the amino acid sequence deduced from the determined base sequence.

The amino acid sequence of said polypeptide has homology of more than 90% with that of rat PDI, but no homology with the amino acid sequence of thyroxine binding globulin (TBG), thyroxine binding prealbumin (TBPA) or C-erbA protein, all of which are capable of binding with thyroid hormone.

Escherichia coli K12 DH5α/pT3BP-2, carrying the plasmid pT3BP-2, has been deposited at the Institute for Fermentation, Osaka (IFO) under the accession number IFO 14563, and has also been deposited at the Fermentation Research Institute (FRI), Agency of Industrial Science and Technology, Ministry of International Trade and Industry, Japan under the accession number FERM BP-1595.

The EcoR I-Pvu II fragment of the cDNA carried by pT3BP-1 can also be obtained by treatment of pT3BP-2 with Kpn I and Sac I followed by treatment with EcoR I and Pvu II.

Example 1

(Isolation of Plasmid Containing Human PDI cDNA and Determination of its Base Sequence)

A λgt11 cDNA library produced on the basis of human placental mRNA (purchased from Toyobo Co., Ltd., Japan), using Escherichia coli Y1096 as the host, was spread on 4 soft agar plates in an amount of about $1 \times 10^5$ clones per plate, and these were transferred to nitrocellulose filters (Millipore's HATF filters). The phages on these filters were then lysed with a 0.5N NaOH solution, and the exposed and denatured phage DNAs were immobilized on the filters while drying (Maniatis, et al.: "Molecular Cloning", Cold Spring Harbor Laboratory, P. 320, 1982). Separately, the DNA fragment obtained by cleaving with the restriction enzymes EcoR I and Pvu II the cDNA portion contained in the plasmid pT3BP-1 described in Reference Example 2 was labeled with $^{32}P$ by the nick translation method (Maniatis et al.: ibid, P. 109, ) for use as the probe.

Hybridization reaction was carried out between the labeled probe and the DNA-immobilized filters in 10 ml of a mixture containing the labeled probe, 5×SSPE [0.9M NaCl, 50 mM sodium phosphate buffer (pH 7.4), 5 mM EDTA], 50% formamide, 5×Denhardt's solution, 0.1% SDS and 100 μg/ml denatured salmon sperm DNA at 42° C. for 16 hours. After the reaction, the filters were washed twice with 2×SSC (1×SSC=0.15M NaCl, 0.015M sodium citrate) -0.1% SDS solution at room temperature for 30 minutes, and further washed twice with 1×SSC-0.1% SDS solution at 68° C. for 30 minutes. After the washed filters were dried, radioautograms were taken, and clones reacting with the probe were picked up. The phage DNA was extracted from the clone thus obtained, namely λgt11 T3BP-3, by the method of Davis et al. (Davis et al.: "Advanced Bacterial Genetics", Cold Spring Harbor Laboratory, 1980). The cDNA was then cut out from λgt11 T3BP-3 with EcoR I, and re-cloned to the EcoR I site in the plasmid pUC19 to thereby construct the plasmid pT3BP-3. *E. coli* K12 DH5α was transformed with the plasmid pT3BP-3; from the obtained transformant, namely *E. coli* K12 DH5α/pT3BP-3, the plasmid pT3BP-3 was extracted and purified by the alkaline extraction method [Birnboim, H. C. and Doly, J.: Nucl. Acids Res., 11, 1513 (1979)]. The cDNA portion contained in this plasmid has a total length of about 2.4 Kbp. FIG. 4 shows a schematized cleavage map with restriction enzymes of the cDNA portion.

The base sequence of this cDNA portion was determined by the dideoxynucleotide chain termination method [Messing, J. et al.: Nucl. Acids Res., 9, 309 (1981)]. FIG. 5 shows the amino acid sequence deduced from the determined base sequence.

The amino acid sequence of said polypeptide has homology of more than 90% with that of rat PDI, but no homology with the amino acid sequence of thyroxine binding globulin (TBG), thyroxine binding prealbumin (TBPA) or C-erbA protein, all of which are capable of binding with thyroid hormone.

*Escherichia coli* K12 DH5α carring the plasmid pT3BP-3 (*Escherichia coli* K12 DH5α/pT3BP-3) has been deposited at the IFO under the accession number IFO 14610, and has also been deposited at the FRI under the accession number FERM BP-1841 (transferred from FERM P-9386).

Example 2

(Construction of Expression Plasmid for Animal Cells)

Figure 6:
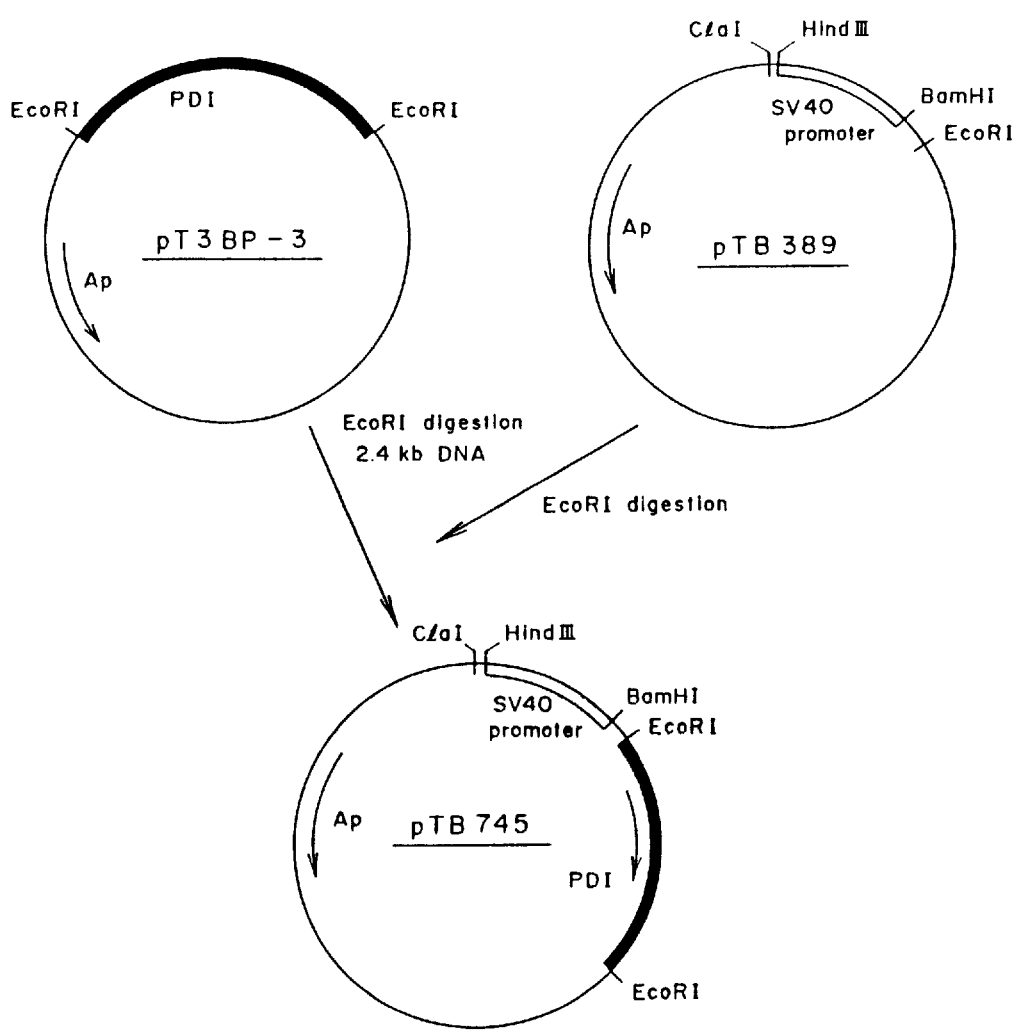
FIG. 6 shows the construction scheme for the plasmid for expression of the human PDI gene in animal cells.

The DNA of the plasmid pT3BP-3 was cleaved with the restriction enzyme EcoR I, to separate the 2.4 Kbp cDNA as shown in FIG. 4. Separately, the plasmid pTB389, which was obtained by converting the Pst I cleavage site in the 5' end side and BamH I cleavage site in the 3' end side in the interleukin-2 gene region of the plasmid pTB106 which was described in Japanese Unexamined Patent Publication No. 63282/1986 into EcoR I sites and eliminating the interleukin-2 gene region, was cleaved with the restriction enzyme EcoR I and the phosphate group in the 5' end thereof was eliminated by alkaline phosphatase treatment. The resulting fragment and the above cDNA were mixed and ligated together by T4 DNA ligase to thereby construct the plasmid pTB745 (FIG. 6).

Example 3

(Expression of Human PDI-encoding Gene in Animal Cells)

Simian COS-7 cells were cultured in the manner of monolayer culture on DMEM medium containing 10% fetal calf serum, and the medium was then replaced with a fresh one of the same medium. Four hours after the exchange of medium, calcium phosphate gel containing 10 μg of the DNA of the plasmid pTB745 was prepared in accordance with a known method [Graham et al.: Virology, 52, 456 (1973)] and added to the cells to thereby give pTB745-infected COS-7 cells. Further 4 hours later, the cells were treated with glycerol, and then cultivation of the pTB745-infected COS-7 cells was continued on a medium containing 0.5% fetal calf serum.

Figure 7A:
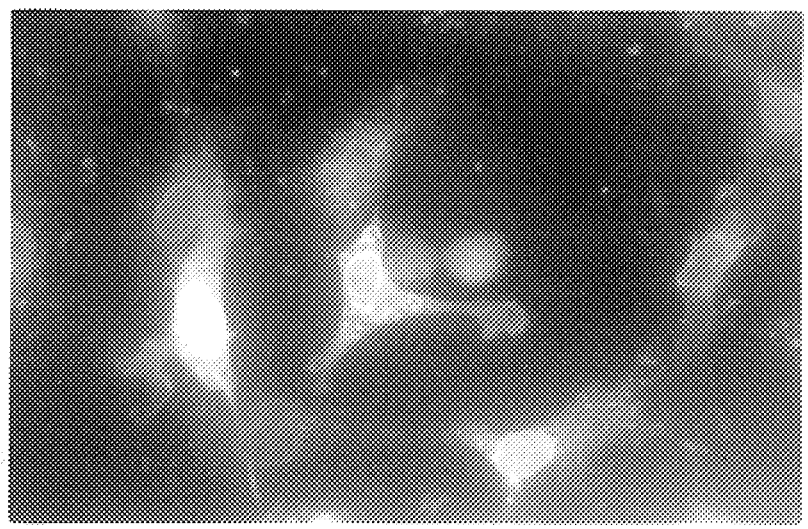
FIGS. 7A and 7B shows the results (fluorescent photomicrographs) of detection by the fluorescent antibody method of human PDI as synthesized in COS-7 cells into which the human PDI gene were introduced.
Figure 7B:
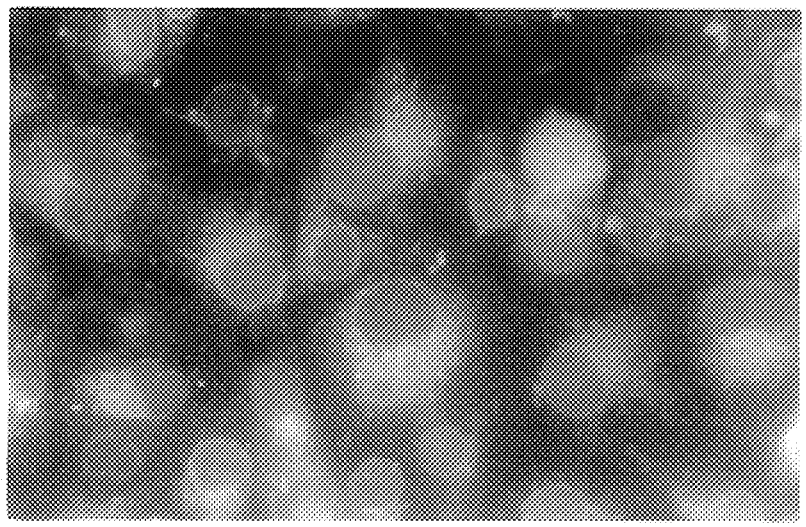

After 48 hours, the pTB745-infected COS-7 cells were fixed with PBS containing 3.5% formalin at room temperature for 15 minutes. The cells were treated with PBS containing 0.1% saponine at room temperature for 10 minutes, and then reacted with the above-mentioned anti-bovine T3BP rabbit antibody at 4° C. for 2 hours. After thoroughly washing out the unreacted antibodies with PBS, FITC-labeled anti-rabbit IgG sheep antibodies were reacted with the cells overnight, and the cells were observed by means of a fluorescence microscope. The results are shown in FIG. 7. Evidently stronger fluorescence was observed in the cells into which the human PDI gene were introduced than in the control COS cells; it was found that human PDI protein was synthesized in the COS cells.

Example 4

(Construction of Plasmid for Expression of Human PDI Gene in *Escherichia coli*)

The plasmid pT3BP-3 obtained in Example 1 as mentioned above and containing the human PDI cDNA was cleaved with the restriction enzyme Ava I, to obtain a 0.85 Kbp DNA fragment containing the first half of the human PDI-encoding region. This DNA fragment was reacted with DNA polymerase (Klenow fragment) in the presence of dATP, dCTP, dGTP and dTTP to thereby render the Ava I cleavage sites blunt. This DNA fragment was ligated with phosphorylated synthetic oligonucleotides, 5'AATTCTATG-GCGC3' and 5'GCGCCATAG3', in the presence of T4 DNA ligase, and cleaved with EcoRI and ClaI to prepare a 0.49 Kbp DNA fragment. Separately, the plasmid pT3BP3 was cleaved with Cla I and Pst I to prepare a 1.47 Kbp DNA fragment containing the second half of the PDI-encoding region. The DNA of the trp promoter-containing plasmid ptrp781 [Kurokawa, T. et al.: Nucleic Acids Res., 11, 3077–3085 (1983)] was cleaved with EcoR I and Pst I, to isolate and an about 3.2 Kbp DNA fragment containing the trp promoter, the tetracycline resistance gene and the plasmid replication origin. This 3.2 Kbp EcoR I-Pst I DNA fragment was ligated with the above-mentioned 0.49 Kbp EcoR I-Cla I DNA fragment containing the human PDI-encoding gene and the 1.47 Kbp Cla I -Pst I DNA fragment by T4 DNA ligase, to construct a human PDI expression plasmid, pTB766 (FIG. 8). This plasmid was used to transform *Escherichia coli* K12 DH1 and MM294 strains to give transformants carrying the plasmid pTB766, namely *Escherichia coli* K12 DH1/pTB766 and MM294/pTB766.

*Escherlchia coli* K12 MM294 carrying the plasmid pTB766 (*Escherichia coli* MM294/pTB766) has been deposited at the IFO under the accession number IFO 14611, and has also been deposited at the FRI under the accession number FERM BP-1842 (transferred from FERM P-9391). *Escherichia coli* K12 DH1 carrying the plasmid ptrp781 (*Escherichia coli* DH1/ptrp781) has been deposited at the IFO under the accession number IFO 14546 and at the FRI under the accession number FERM BP-1591 (transferred from FERM P-9055).

Example 5

(³⁵S-methionine Labeling and Immunoprecipitation Reaction of *Escherichia coli*)

*Escherichia coli* MM294 or DH1 carrying the expression plasmid pTB766 was cultivated in M9 medium containing 8 μg/ml tetracycline, 0.2% casamino acids and 1% glucose at 37° C. When the Klett value was 200, IAA (3β-indolylacrylic acid) was added to a concentration of 25 μg/ml. Two hours later, ³⁵S-methionine was added to an activity of 15 μCi/ml, and the synthesized protein was labeled during the following 30 minutes. After the labeling, the cells were harvested and washed with a 0.15M NaCl solution 10% sucrose solution in 10 mM Tris-HCl, pH 8.0, of one-fifth volume to the culture medium. To this suspension were added phenylmethylsulfonyl fluoride (PMSF) to 1 mM, NaCl to 0.2M and EDTA to 10 mM, and lysozyme was further added to 150 μg/ml. After the reaction was carried out at 0° C. for 1 hour, the suspension was treated at 31° C. for 2 minutes, and then ultrasonicated for a while (about 10 seconds). The sonication product was centrifuged to give a cell extract. To this cell extract was added the anti-bovine T3BP rabbit antibody [Horiuchi, R. and Yamauchi, K.: Gunma Symposia on Endocrinology, 23, 149 (1986)], and the reaction was carried out at 4° C. overnight. Staphylococcal cells (Protein A) were then further added, and the whole mixture was allowed to stand at 0° C. for 3 hours to thereby bind the antigen-antibody conjugate with the cells. The cells were washed repeatedly by centrifugation with a solution of 5 mM EDTA, 150 mM NaCl, 0.05% Nonidet P-40 (Shell Oil) and 1 mg/ml ovalbumin in 50 mM Tris-HCl, pH 7.4, and then treated at 100° C. for 5 minutes in an electrophoresis sample preparation solution (2% SDS, 5% 2-mercaptoethanol, 0.001% bromophenol blue and 10% glycerol in 0.0625M Tris-HCl, pH 6.8) to thereby elute the conjugate. The obtained immunoprecipitate was analyzed by means of 10 to 20% gradient SDS-polyacrylamide gel electrophoresis. After the electrophoresis, the gel was fixed with a 50% trichloroacetic acid solution, and a radioautogram was taken by the fluorography technique. From the results shown in FIG. 9, it is evident that PDI of the expected size (about 60 kDa) was produced in either of the 2 strains carrying the expression plasmid, namely *Escherichia coli* DH1/pTB766 and MM294/pTB766.

Example 6

(Construction of Plasmid for Expression of Human PDI Gene in Yeasts)

Figure 10:
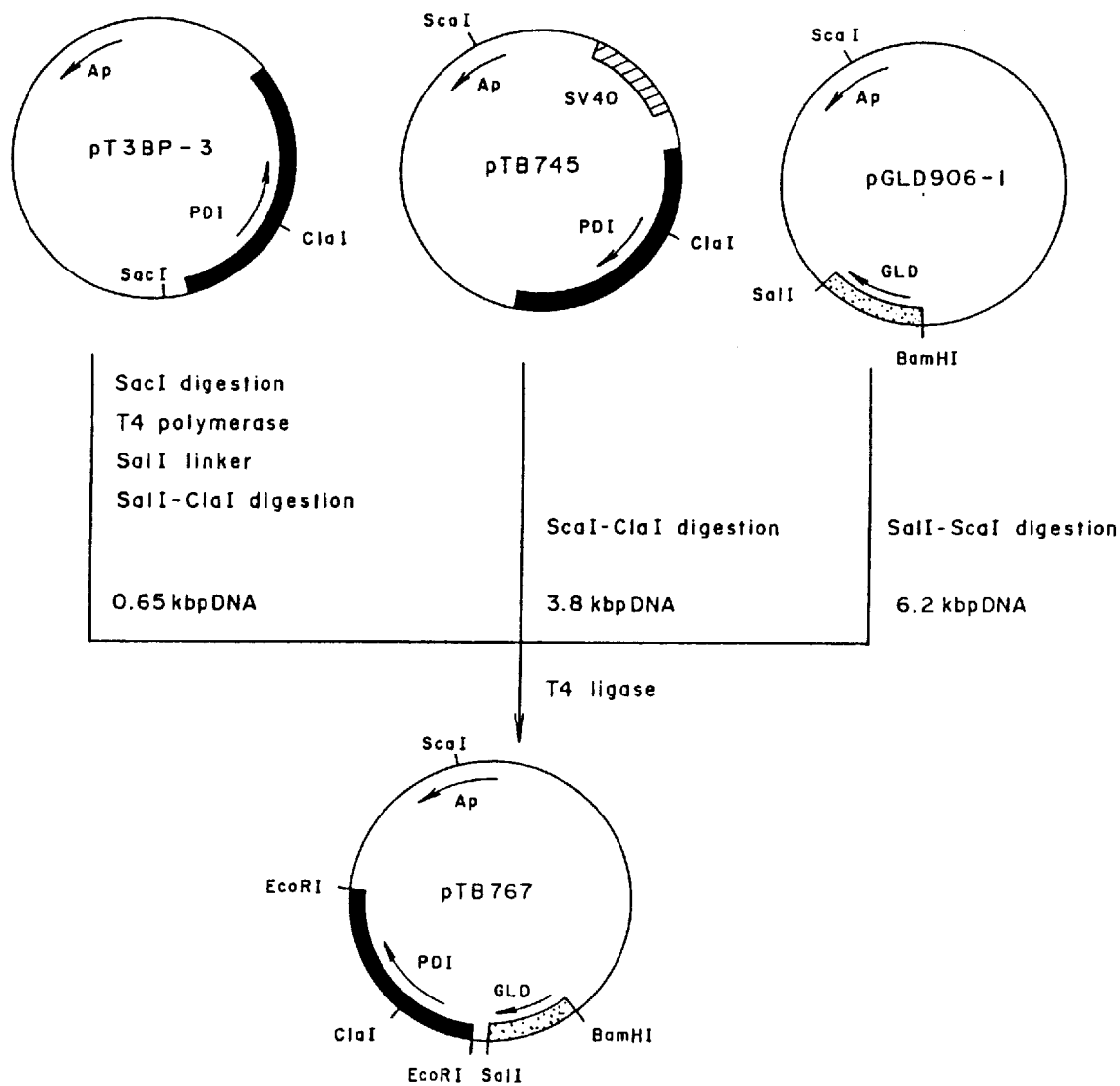
FIG. 10 shows the construction scheme for the plasmid for expression of the human PDI gene in yeasts.

The plasmid pT3BP-3 obtained in Example 1 as mentioned above and containing the human PDI cDNA was digested with the restriction enzyme Sac I and rendered blunt-ended by T4 DNA polymerase reaction. The Sal I linker GGTCGACC was joined to the above cleavage product. The ligation product was further digested with the restriction enzymes Sal I and Cla I, to prepare a 0.65 Kbp DNA fragment. Also, the DNA of the plasmid pTB745 described in Example 2 was digested with the restriction enzymes Sca I and Cla I, to isolate a 3.8 Kbp DNA fragment. Further, the DNA of the plasmid pGLD906-1 [Biochem. Biophys. Res. Commun., 138, 268 (1986)] was digested with the restriction enzymes Sal I and Sca I, to prepare a 6.2 Kbp DNA fragment. This DNA fragment was ligated with the above-mentioned 2 DNA fragments by means of T4 DNA ligase, to construct a plasmid for expression in yeasts, pTB767 (FIG. 10). This plasmid was used to transform AH22R-strain to give a yeast strain carrying the plasmid pTB767, namely *Saccharomyces cerevisiae* AH22R⁻/pTB767.

*Saccharomyces cerevisiae* AH22R⁻ carrying the plasmid pTB767 (*Saccharomyces cerevisiae* AH22R⁻/pTB767) has been deposited at the IFO under the accession number IFO 10425, and has also been deposited at the FRI under the accession number FERM BP-1843 (transferred from FERM P-9603).

Example 7

(³⁵S-methionine Labeling and Immunoprecipitation Reaction of Yeast)

The yeast strain AH22R⁻ carrying the expression plasmid pTB767 was cultivated in low-Pi medium [Biochem. Biophys. Res. Commun., 138, 268 (1986)] at 37° C. overnight, and then ³⁵S-methionine was added to 20 μCi/ml to label the synthesized protein. After the labeling, the cells were harvested and washed with a 0.15M NaCl solution, and 7M guanidine hydrochloride of one-fifth volume to the culture medium was added. After the cells were lysed at 0° C. for 1 hour, the lysate was centrifuged at 10,000 rpm for 10 minutes. The resulting supernatant was dialyzed against a solution containing 10 mM Tris.HCl (pH 8.0), 1 mM EDTA, 200 mM NaCl and 1 mM PMSF to give a cell extract. To this cell extract was added the anti-bovine T3BP rabbit antibody (described in Example 5), and then the procedure described in Example 5 was taken to give an immunoprecipitate, which was then analyzed by SDS-polyacrylamide gel electrophoresis and radioautography. As a result, there was synthesized a polypeptide specific to the yeast strain AH22R⁻/pTB767 carrying the expression plasmid; it was demonstrated that human PDI was produced in the yeast.

The composition of the used low-Pi medium was as follows: Low-Pi medium [per 1 l]

| | |
|---|---|
| KCl | 1.5 g |
| Glucose | 20 g |
| Asparagine | 2 g |
| L-histidine | 100 mg |
| KI(1 mg/ml) | 100 ul |
| MgSO₄.7H₂O (500 mg/10 ml) | 10 ml |
| CaCl₂.2H₂O (330 mg/10 ml) | 10 ml |
| Trace element solution (a) | 1 ml |
| Vitamine solution (b) | 1 ml |
| Trace element solution (a) [per 1 l] | |
| CuSO₄.5H₂O) | 40 mg |
| FeSO₄.7H₂O) | 250 mg |
| MnSO₄.4H₂O) | 40 mg |
| (NH₄)₃PO₄.12MoO₃.3H₂O) | 20 mg |
| ZnSO₄.7H₂O | 310 mg |
| Vitamine solution (b) [per 1 l] | |
| Inositol | 10 g |
| Thiamine | 200 mg |
| Pyridoxine | 200 mg |
| Calcium pantothenate | 200 mg |
| Niacin | 200 mg |
| Biotin | 2 mg |

Example 8

(Purification of PDI Derived From *Escherichia coli* MM294/pTB766)

*Escherichia coli* MM294 carrying the expression plasmid pTB766 obtained in Example 4 was cultivated in 1-liter of a medium containing 5 mg/l tetracycline, 10 g/l Bactotrypton, 5 g/l Bacto-yeast extrafct and 5 g/l NaCl at 37° C. for 11 hours. The culture was then transferred to 20-liter of M-9 medium containing 2 mg/l vitamine B₁, 10 g/l glucose and 10 g/l casamino acids, and the culture was maintained with agitation and aeration at 37° C. for further 9 hours. After cultivation, the cells (385 g by wet weight) were collected by centrifugation and stored at −80° C. until used.

The cells (30 g by wet weight) were suspended in 150 ml of 20 mM Tris-HCl buffer (pH 7.4) containing 0.15M NaCl, 10 mM ethylenediaminetetraacetic acid (EDTA), 1 mM phenylmethylsulfonyl fluoride (PMSF), and 0.1 mM (p-amidinophenyl)methanesulfonyl fluoride-HC1 (APMSF). The suspension was subjected to successive sonication (1 min×4 times) at 0° C. and centrifuged to give 156 ml of a crude extract.

The crude extract was applied to a Cellulofine GCL-2000-sf (Seikagaku Kogyo Co., Ltd., Tokyo, Japan) column (6×102 cm, 2880 ml) which had been previously equilibrated with 10 mM sodium phosphate buffer (pH 6.8) containing 0.15N NaCl, 1 mM $CaCl_2$ and 0.1 mM APMSF. The column was developed with the same buffer and the eluates (325 ml) containing PDI were collected.

The eluates thus obtained were applied to a hydroxyapatite (Bio-Rad, California, U.S.A.) column (1.5×14 cm, 25 ml) which had been previously equilibrated with 10 mM sodium phosphate buffer (pH 6.8) containing 0.145M NaCl, 1 mM $CaCl_2$ and 0.1 mM APMSF. The column was washed with the same buffer and then developed with a linear gradient of sodium phosphate concentration. The gradient was produced by adding 200 ml of 300 mM sodium phosphate buffer (pH 6.8) to 200 ml of 10 mM sodium phosphate buffer (pH 6.8). Eluates containing PDI were collected.

The eluates were dialyzed overnight against 10 mM sodium phosphate buffer (pH 6.8) containing 0.1 mM APMSF. The dialyzed solution was then applied to a DEAE-Toyopearl (Tosoh, Tokyo, Japan) column (1.5×15 cm, 26.5 ml) equilibrated with the same buffer. The column was washed with the same buffer and then developed with a linear gradient of NaCl concentration. The gradient was produced by adding 200 ml of 10 mM sodium phosphate buffer (pH 6.8) containing 0.5M NaCl and 0.1 mM APMSF to 200 ml of 10 mM sodium phosphate buffer (pH 6.8) containing 0.1 mM APMSF. Fractions containing PDI were collected.

The fractions containing PDI were dialyzed against 10 mM sodium phosphate buffer (pH 6.8) containing 0.1 mM APMSF. The dialyzed solution was applied to a DEAE-NPR HPLC column (Tosoh, Tokyo, Japan; 0.46×3.5 cm) which had been previously equilibrated with 10 mM sodium phosphate buffer (pH 6.8) containing 0.09M NaCl. Proteins were eluted by increasing the NaCl concentration from 0.09M to 0.39M in a period of 30 minutes. Fractions containing PDI were collected and sterilized by filtration. Protein concentration, 106 μg/ml; total volume, 17.1 ml; total protein, 1.8 mg.

Figures 9, 11:
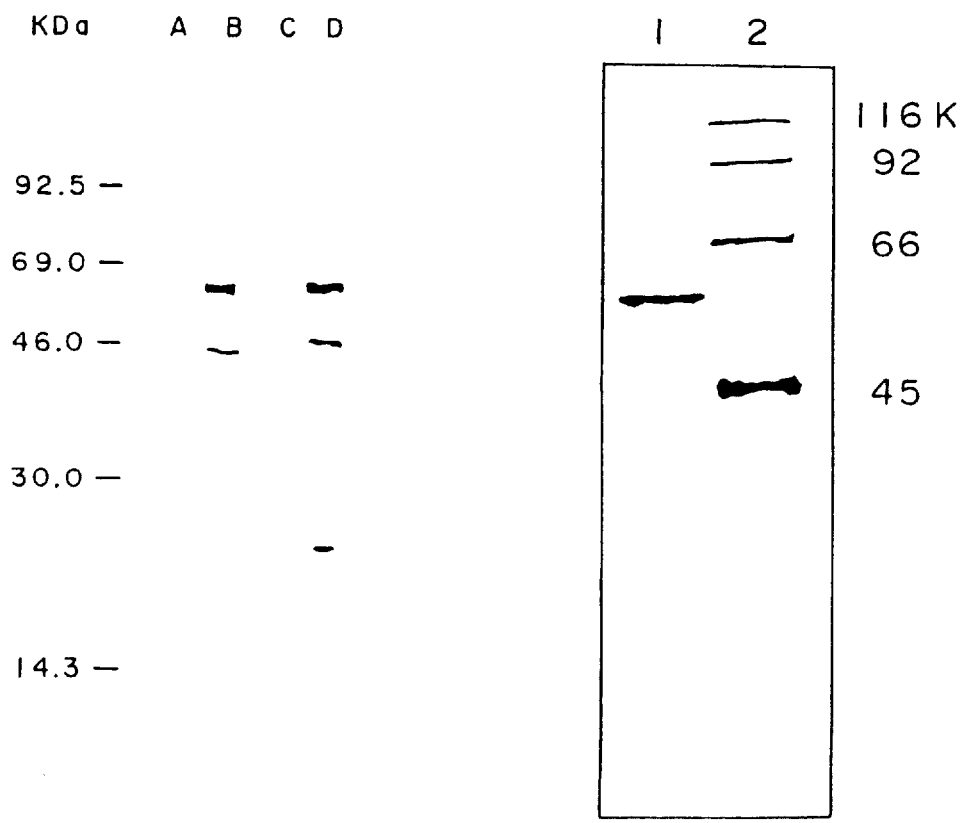
FIG. 9 shows the elution pattern of human PDI produced in *Escherichia coli* as obtained by the immunoprecipitation method.
FIG. 11 shows SDS-polyacrylamide gel electrophoresis of PDI. Lane 1 and Lane 2 correspond to purified PDI and marker proteins, respectively.

The final preparation thus obtained was homogeneous as judged by SDS-polyacrylamide gel electrophoresis (FIG. 11).

Example 9

(Alternative Purification Method for PDI Derived From *Escherichia coli* MM294/pTB766)

*E. coli* cells (30 g) obtained in Example 8 were suspended in 160 ml of 20 mM Tris-HCl buffer (pH 7.4) containing 0.15M NaCl, 10 mM EDTA, 1 mM PMSF and 0.1 mM APMSF. The cells were disrupted at 0° C. for 30 minutes by glass beads with a diameter of 0.25 to 0.5 mm using a Bead-Beater (Biospec Products Inc., U.S.A.). The suspension was centrifuged and the supernatant fluid (84 ml) was collected.

The supernatant fluid was successively subjected to the same purification procedures described in Example 8 to give a homogeneous PDI preparation. Protein concentration, 111 μg/ml; total volume, 9.0 ml; total protein, 1.0 mg.

Example 10

(Protein-chemical Characterisations of PDI)

The PDI preparation obtained in Example 8 was subjected to the following protein-chemical analyses.

(1) Molecular weight:

PDI was subjected to SDS-polyacrylamide gel electrophoresis under reducing conditions [Nature 227, 680 (1970)] and the proteins were stained with Coomassie Brilliant Blue R-250. PDI showed a single band with an approximate molecular weight of 55,000 (FIG. 11).

(2) Amino acid composition:

The amino acid composition was determined on 24, 48 and 72-hour hydrolysates with 6N-HCl at 110° C. in the presence of 4% thioglycolic acid. Amino acid analysis was performed by the ninhydrin method in a Hitachi amino acid analyzer model 835. The values of Ser and Thr were obtained by extrapolating to zero time hydrolysis, and H-Cys (half cystine) was determined as cysteic acid on a 24-hour hydrolysate after performic acid oxidation. The amino acid composition agreed well with that deduced from the cDNA base sequence as shown in Table 2.

TABLE 2

| Amino acid | Number of residues per molecule | Values predicted from cDNA sequence |
| --- | --- | --- |
| Asp/Asn | 54.4 | 57 |
| Thr | 21.8 | 23 |
| Ser | 21.2 | 23 |
| Glu/Gln | 70.7 | 69 |
| Pro | 20.5 | 21 |
| Gly | 29.5 | 29 |
| Ala | 46.6 | 44 |
| H-Cys | 5.5 | 6 |
| Val | 31.1 | 29 |
| Met | 4.5 | 5 |
| Ile | 21.5 | 23 |
| Leu | 41.5 | 41 |
| Tyr | 11.9 | 12 |
| Phe | 34.0 | 33 |
| Lys | 46.6 | 47 |
| His | 11.7 | 11 |
| Arg | 13.6 | 13 |
| Trp | 4.5 | 5 |

(3) Amino terminal amino acid sequence:

The sequence analysis of PDI (102 μg; 1.85 nmole) was performed in a gas-phase protein sequencer (model 470A, Applied Biosystems, California, U.S.A.). Phenylthiohydantoin (PTH)-amino acid was determined by HPLC on a Micropak SP-ODS column (varian, U.S.A.). The sequence was identical with that deduced from cDNA up to 20 cycles as shown in Table 3. Residue numbers 8 and 13 were not identified.

TABLE 3

| | PTH-amino acid detected | | Amino acid predicted |
| --- | --- | --- | --- |
| Cycle | Residue | pmole | from cDNA sequence |
| 1 | Met | 373 | (Met) |
| 2 | Ala | 720 | Ala |

TABLE 3-continued

| | PTH-amino acid detected | | Amino acid predicted |
|---|---|---|---|
| Cycle | Residue | pmole | from cDNA sequence |
| 3 | Pro | 277 | Pro |
| 4 | Glu | 319 | Glu |
| 5 | Glu | 379 | Glu |
| 6 | Glu | 353 | Glu |
| 7 | Asp | 303 | Asp |
| 8 | — | — | His |
| 9 | Val | 271 | Val |
| 10 | Leu | 581 | Leu |
| 11 | Val | 333 | Val |
| 12 | Leu | 638 | Leu |
| 13 | — | — | Arg |
| 14 | Lys | 227 | Lys |
| 15 | Ser | 92 | Ser |
| 16 | Asn | 257 | Asn |
| 17 | Phe | 330 | Phe |
| 18 | Ala | 615 | Ala |
| 19 | Glu | 334 | Glu |
| 20 | Ala | 669 | Ala |

(4) Carboxyl terminal amino acid:

The carboxyl terminal amino acid of PDI (151 μg; 2.75 nmoles) was hydrazinolysis [J. Biochem., 59, 170 (1966)] and the amino acid s determined by amino acid analysis. The carboxyl terminal thus determined was leucine. The recovery was 46%.

Figure 12:
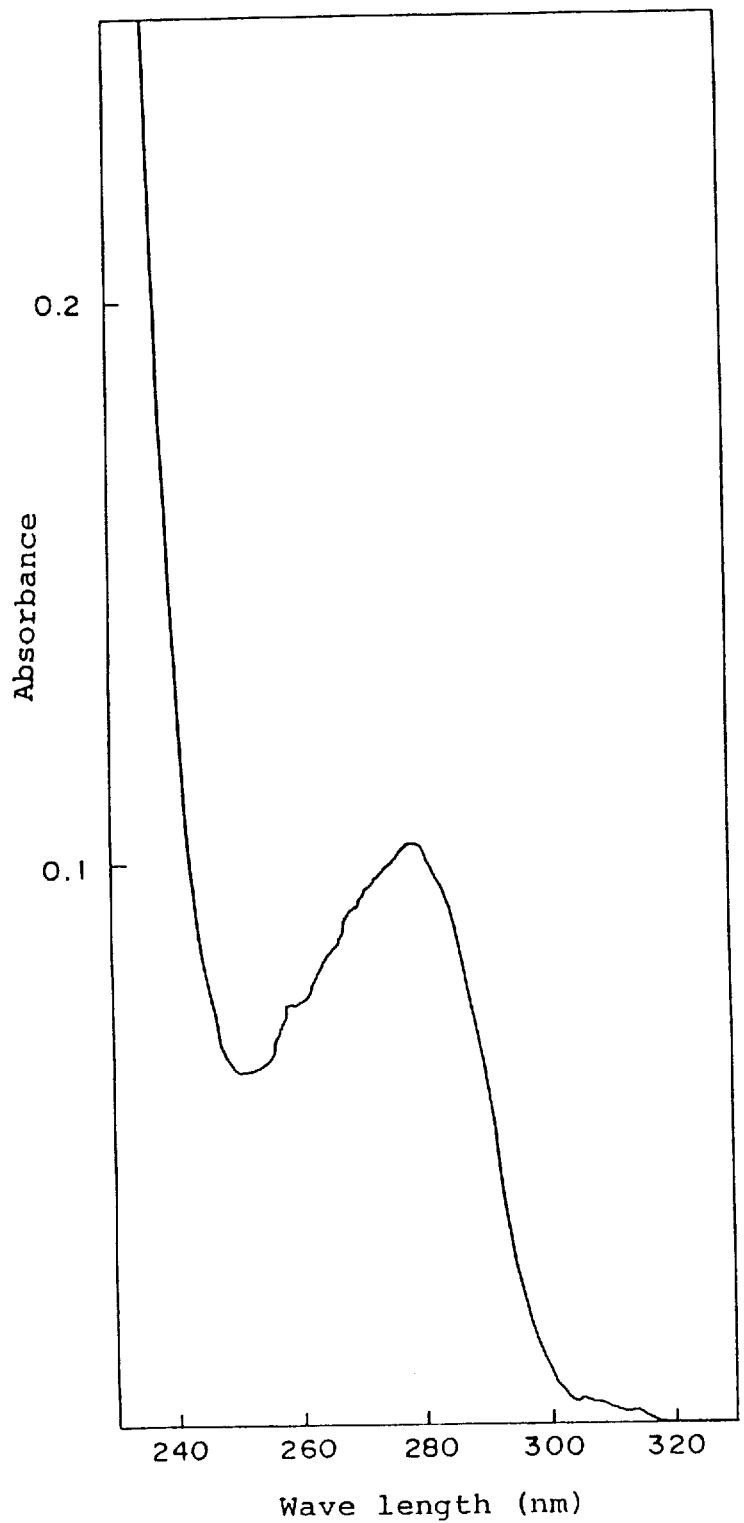
FIG. 12 shows ultraviolet absorption spectrum of purified PDI.

(5) Ultraviolet (UV) absorption spectrum:

PDI showed an UV absorption spectrum with a peak absorption at 280 nm in 10 mM sodium phosphate buffer (pH 6.8) (FIG. 12).

Example 11

(Refolding of Scrambled Ribonuclease (RNase) by PDI)

The enzymatic activity of PDI obtained in Example 8 was determined by its ability to refold scrambled RNase in the presence of dithiothreitol (DTT).

(1) PDI:

The homogeneous preparation obtained in Example 8 was used.

(2) Scrambled RNase:

Scrambled RNase was prepared according to the method of Hillson et al. [Methods in Enzymology 107, 281–284 (1984)] starting from bovine pancreatic RNase.

(3) Determination of RNase activity:

The activity of RNase was determined by the method of Kalnisky et al. [J. Biol. Chem., 234, 1512–1516 (1959)] with yeast poly RNA as substrate.

(4) Buffers:

Buffer A: 100 mM sodium phosphate buffer (pH 7.8) containing 10 mM EDTA; buffer B: 0.2M sodium acetate buffer (pH 5.0); buffer C: 0.1M sodium acetate buffer (pH 5.0).

(5) Refolding of scrambled RNase:

A test tube containing 10 μl of PDI (111 μg/ml), 168 μl of buffer A and 2 μl of 1 mM DTT was placed in a water bath of 30° C. and preincubated for 5 minutes. Twenty (20) μl of scrambled RNase (0.5 mg/ml) was added to the test tube and the whole reaction mixture was kept at 30° C. for 60 minutes. The reaction was terminated by adding 800 μl of buffer B.

Refolded and active RNase formed in the reaction mixture was determined as follows: Two hundred (200) μl of the above reaction mixture was transferred to a centrifuge tube and preincubated at 37° C. for 5 minutes. Two hundred (200) μl of 1% yeast poly RNA which had been preincubated at 37° C. for 5 minutes was added to the reaction mixture in the centrifuge tube and the whole mixture was kept at 37° C. for 4 minutes. Two hundred (200) μl of 25% perchloric acid solution containing 0.75% uranium acetate was added to the reaction mixture and the whole mixture was incubated in a ice-water bath for 5 minutes and centrifuged at 16,000 rpm for 5 minutes. The supernatant fluid was diluted thirty-fold with distilled water and the absorbance at 260 nm was determined.

PDI caused the refolding of scrambled RNase in the presence of $1 \times 10^{-5}$M DTT: About 25% of the scrambled RNase was converted into an active and refolded form under the experimental conditions employed (Table 4).

TABLE 4

| Addition | RNase activity (%) |
|---|---|
| None | 0.9 |
| PDI | 0.9 |
| DTT | 4.4 |
| PDI + DTT | 24.9 |

Example 12

(Refolding of Scrambled Recombinant Interleukin-2 (rIL-2) by PDI)

PDI obtained in Example 8 was added to a scrambled rIL-2 solution and the refolding of scrambled rIL-2 was determined by the increase of IL-2 activity.

(1) Scrambled rIL-2:

Scrambled rIL-2 was prepared according to the method of Brawning et al. [Anal. Biochem., 155, 123–128 (1986)] starting from homogeneous rIL-2 [Kato et al., Biochem. Biophys. Res. Commun., 130, 692–699 (1985)]. Scrambled rIL-2 is known to possess little biological activity [Brawning et al., Anal. Biochem., 155, 123–128 (1986)].

(2) Determination of IL-2 activity.

Biological activity of IL-2 was determined by the modified MTT method using mouse NKC3 cells reported by Tada et al. [J. Immunol. Methods, 93, 157–165 (1986)].

(3) Refolding of scrambled rIL-2:

One hundred and fifty (150) μl of scrambled rIL-2 (200 μg/ml) was added to a test tube containing varying amount of PDI (final concentration of 0, 0.74, 1.85 and 3.70 μg/ml), 1000 μl of 30 mM Tris-acetate buffer (pH 9.0), 30 μl of 1 mM DTT and distilled water in a final volume of 2850 μl. The whole reaction mixture was incubated at 30° C. for 18 hours. IL-2 activity was determined for each tube by the modified MTT method.

Native rIL-2 was increased with the increase of PDI concentration added to the reaction mixture (Table 5).

TABLE 5

| PDI added (μg/ml) | Active IL-2 (μg/ml) |
|---|---|
| 0 | 1.28 |
| 0.74 | 2.37 |
| 1.85 | 2.77 |
| 3.70 | 3.02 |

What is claimed is:

1. An isolated polypeptide comprising the amino acid sequence of FIG. 3.

2. The polypeptide according to claim 1, which is produced by a recombinant microorganism.

3. The polypeptide according to claim 2, wherein the microorganism is *Escherichia coli*.

4. The polypeptide according to claim 1, which comprises the amino acid sequence:

MetAlaProGluGluGluAspHisValLeuValLeuArgLysSerAsnPheAlaGluAla

LeuAlaAlaHisLysTyrLeuLeuValGluPheTyrAlaProTrpCysGlyHisCysLys

AlaLeuAlaProGluTyrAlaLysAlaAlaGlyLysLeuLysAlaGluGlySerGluIle

ArgLeuAlaLysValAspAlaThrGluGluSerAspLeuAlaGlnGlnTyrGlyValArg

GlyTyrProThrIleLysPhePheArgAsnGlyAspThrAlaSerProLysGlyTyrThr

AlaGlyArgGluAlaAspAspIleValAsnTrpLeuLysLysArgThrGlyProAlaAla

ThrThrLeuProAspGlyAlaAlaAlaGluSerLeuValGluSerSerGluValAlaVal

IleGlyPhePheLysAspValGluSerAspSerAlaLysGlnPheLeuGlnAlaAlaGlu

AlaIleAspAspIleProPheGlyIleThrSerAsnSerAspValPheSerLysTyrGln

LeuAspLysAspGlyValValLeuPheLysLysPheAspGluGlyArgAsnAsnPheGlu

GlyGluValThrLysGluAsnLeuLeuAspPheIleLysHisAsnGlnLeuProLeuVal

IleGluPheThrGluGlnThrAlaProLysIlePheGlyGlyGluIleLysThrHisIle

LeuLeuPheLeuProLysSerValSerAspTyrAspGlyLysLeuSerAsnPheLysThr

AlaAlaGluSerPheLysGlyLysIleLeuPheIlePheIleAspSerAspHisThrAsp

AsnGlnArgIleLeuGluPhePheGlyLeuLysLysGluGluCysProAlaValArgLeu

IleThrLeuGluGluGluMetThrLysTyrLysProGluSerGluGluLeuThrAlaGlu

ArgIleThrGluPheCysHisArgPheLeuGluGlyLysIleLysProHisLeuMetSer

GlnGluLeuProGluAspTrpAspLysGlnProValLysValLeuValGlyLysAsnPhe

GluAspValAlaPheAspGluLysLysAsnValPheValGluPheTyrAlaProTrpCys

GlyHisCysLysGlnLeuAlaProIleTrpAspLysLeuGlyGluThrTyrLysAspHis

GluAsnIleValIleAlaLysMetAspSerThrAlaAsnGluValGluAlaValLysVal

HisSerPheProThrLeuLysPhePheProAlaSerAlaAspArgThrValIleAspTyr

AsnGlyGluArgThrLeuAspGlyPheLysLysPheLeuGluSerGlyGlyGlnAspGly

AlaGlyAspAspAspAspLeuGluAspLeuGluGluAlaGluGluProAspMetGluGlu

AspAspAspGlnLysAlaValLysAspGlyLeu.

5. A method for producing a protein of a eukaryotic organism having a natural type disulfide bond in its molecule, which comprises subjecting a protein of a eukaryotic organism produced from a recombinant prokaryotic cell, to a reaction with a polypeptide comprising the amino acid sequence of FIG. 3.

6. The method according to claim 5, wherein the reaction is carried out in the presence of a reducing agent.

* * * * *